United States Patent
Bhatti et al.

(10) Patent No.: US 9,394,576 B2
(45) Date of Patent: Jul. 19, 2016

(54) METHODS AND COMPOSITIONS TO SELECT COTTON PLANTS RESISTANT TO COTTON ROOT KNOT NEMATODE

(71) Applicant: Monsanto Technology LLC, St. Louis, MO (US)

(72) Inventors: Muhammad Bhatti, Ballwin, MO (US); Roy G. Cantrell, St. Peters, MO (US); Jinhua Xiao, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 68 days.

(21) Appl. No.: 14/102,357

(22) Filed: Dec. 10, 2013

(65) Prior Publication Data

US 2014/0141430 A1    May 22, 2014

Related U.S. Application Data

(62) Division of application No. 13/059,135, filed as application No. PCT/US2009/055019 on Aug. 26, 2009, now abandoned.

(60) Provisional application No. 61/092,649, filed on Aug. 28, 2008.

(51) Int. Cl.
*C12Q 1/68* (2006.01)
*A01H 1/04* (2006.01)
*A01H 5/10* (2006.01)

(52) U.S. Cl.
CPC ........... *C12Q 1/6895* (2013.01); *A01H 1/04* (2013.01); *A01H 5/10* (2013.01)

(58) Field of Classification Search
None
See application file for complete search history.

(56) References Cited

PUBLICATIONS

Xinlian Shen et al. (Theor. Appl. Genet., (2006), pp. 1539-1549).*
Gupta et al. (Current Science, (2001), pp. 524-535).*
Meksem et al. (Mol. Genet. Genomics, (2001), pp. 207-214).*
Xinlian et al., "QTL mapping for resistance to root-knot nematodes in the M-120 RNR Upland cotton line (*Gossypium hirsutum* L.) of the Auburn 623 RNR source," *Theoretical and Applied Genetics: International Journal of Plant Breeding Research* 113(8):1539-1549, 2006.
Congli et al., "A transgressive segregation factor (RKN2) in *Gossypium barbadenie* for nematode resistance clusters with gene rkn1 in *G. hirsutum*," *Molecular Genetics and Genomics* 279(1):41-52, 2007.
Ynturi et al., "Association of root-knot nematode resistance genes with simple sequence repeat markers on two chromosomes in cotton," *Crop Science* 46(6):2670-2676, 2006.
Wang et al., "Identification and mapping of microsatellite markers liked to a root-knot nematode resistance gene (rkn1) in Acala NemX cotton (*Gossypium hirsutum* L.)," *Theoretical and Applied Genetics: International Journal of Plant Breeding Research* 112(4):770-77, 2006.
Niu et al., "Identification to molecular markers associated with root-knot nematode resistance in upland cotton," *Crop Science* 47(3):951-960, 2007.

* cited by examiner

*Primary Examiner* — Brent Page
*Assistant Examiner* — Jared Shapiro
(74) *Attorney, Agent, or Firm* — Dentons US LLP; Lawrence Lavin Esq.

(57) ABSTRACT

The present invention is in the field of plant breeding and disease resistance. More specifically, the invention provides a method for breeding cotton plants containing one or more quantitative trait loci that are associated with resistance to Root Knot Nematode (RKN), a disease associated with *Meloidogyne incognita*. The invention further provides germplasm and the use of germplasm containing quantitative trait loci (QTL) conferring disease resistance for introgression into elite germplasm in a breeding program, thus producing novel elite germplasm comprising one or more RKN resistance QTL.

9 Claims, No Drawings

SEQUENCE LISTING

<160> NUMBER OF SEQ ID NOS: 103

<210> SEQ ID NO 1
<211> LENGTH: 643
<212> TYPE: DNA
<213> ORGANISM: Gossypium hirsutum
<220> FEATURE:
<221> NAME/KEY: n = a, t, c, or g
<222> LOCATION: (1)..(643)

<223> OTHER INFORMATION: n = a, t, c, or g

<400> SEQUENCE: 1

```
gttncncctt cctacctcct gttacaattt ttggtacttt ctcttcaatt cccttgagtt      60
ctgaaatata gttattgatg aaacttgcta tctctttccc ggtcctgttg gccttcttat     120
gaactctctt gtttctttct tcccagattg cccaaagagc gcagcaaaag atcctacacc     180
gcgaagaagt gttctgttca aaacccagg tgagccactg ttgaaactcc atctgagata      240
cgtgtaataa ctccaaaaat gataattctt tccatactga tattgagaca gggcattcac     300
ggaatagatg attcgtggtt tctgctgctc ttccacaccc agaacagagt gcattgtgta     360
atagcctttt atgtagcaag gtagtcattg taggtagata attccatgat attctccaaa     420
ctataatttt tatcttagaa gatagattaa gtagccaaag attttttgtaa aaattccatat    480
agtcggtctg taaagcataa gctttaggat caatttcatt gccctgtaat agtttatagg     540
cactatgcac cgtgaattct cctgaaggca ctctgctcca ggccaaaaaa tcatcgtgga     600
cctcttttgc taacggaata tagagaatct tctcagttac atc                        643
```

<210> SEQ ID NO 2
<211> LENGTH: 599
<212> TYPE: DNA
<213> ORGANISM: Gossypium hirsutum

<400> SEQUENCE: 2

```
tcggacaaag ataattagat gcagaaaaaa caattcacct tgaagagaac atgaaagaaa      60
caagtcttgg ggttggcata attttcaaca ggaggctgca caagaacaaa acatttaaa     120
atcaatatat aagcaatcaa accagtaccc caagtacaaa ataaacagct ggatctgaaa     180
ttagtaacat ttctatctaa tttttcatgtt ccgaacaagt atacaatggc catataagca     240
aatgggaact ctattttgtt caatttcatc atctttcttc aaccaaaaca ttgaggaaaa     300
cataaagttg aaatctttac cggctaaagt tggatcttgg gatctaattt gaataaccca     360
gagttgacta ttgaaattgt gtttagaaat ggttagtttt catctgtttt atcaaaaacc     420
aatcaaaagg gtaccgttca aaatcgaaat ctctcacaaa aaactcagat ctaccagtca     480
aacagtccaa tacgtagaac aaatagttac aaatttgata aaccagcaaa aggaaactga     540
agggaaggag aaacagagag agggatcaac tcacctgact aaaatccatt acgggaaga      599
```

<210> SEQ ID NO 3
<211> LENGTH: 960
<212> TYPE: DNA
<213> ORGANISM: Gossypium hirsutum

<400> SEQUENCE: 3

```
tgcagagatc ttcttcagcc attcaatcca gttccaaagt ttatcatcat aaaatctgtg      60
gttttcttaa cctattggca ggtaaaaatct tgtgtgcctg ttatttcctc tcatactcat     120
gcatgcaaaa agaagacaaa tcctttgttt ttggcttta gatacttta tctttccttc       180
tatttcattg catcaccctt ttgttgcttt ttggtgataa tcatcattta gaaatcttgt     240
tagtatcttt atagcaaacc ttggggatgg tgaattctgg ttactggaat gcaatctttc     300
ctaacctgtt tgctgtccac attgatatca tcttcatgtt ttgttttata ggggaggctg     360
tttttctata ttttgctttc cctttttata ctgatgtcta atcataagac agcagttcga     420
agttccggaa gtgctgtgac ggcattgtac aatgtattaa accctgtaaa atagaatgca     480
tgcctatatt gatggttatc cataacatct tgtgttgtga tggcattgta ctgtttgtaa     540
```

| | | |
|---|---|---|
| acctcatcta gttgcatagg tgctaaataa actcaaaaca tccttttctt ttatttcctt | 600 |
| ttgcagggtg ttatgttttt tcttgctgca aaatctggat ttattaagga tgctgatgca | 660 |
| gcagctcaat ttcaaaactt cattatatgt gttgagatgc ttctagctgc tctaggtcat | 720 |
| ctttatgcat ttccatataa ggagtatgct ggtgcaaata ttggtatgtc tcgtggtttt | 780 |
| acacgaagcc ttgcacatgc cttgatgttg aatgacttct atcatgatac tgttcaccag | 840 |
| gtgacccttaa cttctgttgc catttcccaa aggttcctct actggattct tcttcttttg | 900 |
| tttagggtta tttatggttt ttatcatatt cgcagtttgc acctacgtat catgattatg | 960 |

<210> SEQ ID NO 4
<211> LENGTH: 654
<212> TYPE: DNA
<213> ORGANISM: Gossypium hirsutum

<400> SEQUENCE: 4

| | | |
|---|---|---|
| aatctgaaat atgtgacatg cccagatgag atagtatatc attcatactc taccaagtca | 60 |
| tggttccctt aaaaaataat ataggaaacc atttttgtac ctgatcagat catgagtccc | 120 |
| accagatata gcatttgaga tggcttgtgt agcttgtatc caaatatcat atttatcatc | 180 |
| attttgaagc aaatgaagta gaggagcaat aatattagct tcaattatag cctgtaaaat | 240 |
| tcataccatt acccatcgtt tcattgcaca agtcaacgca gataaaacct taggttcaaa | 300 |
| attgatactt gtacctttat ttcctgttgt gatacttgag attgtccaac aagcaaactt | 360 |
| attgattctc ttttcataat tattttcaa aggtttaaaa ggcatgggaa tgcctgatga | 420 |
| ttaatgatac actttgtagc aacaagattt gcccataaat aagaaaataa atcatcttta | 480 |
| acaactaaac ctaaaaaaat ctttagtcta attaagaggg ggtataaatg tgattttagt | 540 |
| gagaaaatta gttattaaaa gaaatgata tgataaatgg aaagagatac atattctagt | 600 |
| aagatcattt aaaaggaaaa gcaaattaaa taaagtgcct gatacctgaa tttg | 654 |

<210> SEQ ID NO 5
<211> LENGTH: 503
<212> TYPE: DNA
<213> ORGANISM: Gossypium hirsutum

<400> SEQUENCE: 5

| | | |
|---|---|---|
| cacaagggca ggctcactag gaatactaca gtactgaagt attctctcaa cagatataat | 60 |
| tttattctcc atactgcaaa tattccatac cacccaagcc agcaacatat ttagattgag | 120 |
| tccatacgtc acagctaaac cggcaatagc taaacaaaag aaaatgcat aaagtcattc | 180 |
| tcctagaaca tttgctatct agtagtcaat aaagctgcca atatgaatct gcatttactt | 240 |
| accaggatcg ataattccct caggtataga gattaaaaag aataaagaga aggcaaacat | 300 |
| aacagaagac agtaagtcca ggcggaagca cagccattcc attgcaccgc aaacatggaa | 360 |
| ttttggacga gaatacgagt cagtcagcac catattggtg tcttggaacc tttctcttg | 420 |
| atcaaagctc cttatagttg ttgctcctaa aattgtttca gcaaaattct ggattactgg | 480 |
| agctttgcat actccaacca acc | 503 |

<210> SEQ ID NO 6
<211> LENGTH: 591
<212> TYPE: DNA
<213> ORGANISM: Gossypium hirsutum

<400> SEQUENCE: 6

```
gaatgcctca cttgcctaat ttattgcttt gactctttgt tgtatgctat ttgactttta      60
accaccatcg aatataaata tataattatt acaaatagtt tagaagatta aataattata     120
tttatattca acccttttga atattcctcg gaaagttctt tgaacaaagc acaaaccatg     180
aaggttacct gtgctcgtca agaagaaacc acgaaatttc actgtttcac accaaagctc     240
caccaccaag tttcccaatt ctaaccaatt ttgattaaac tgagattttc ccaatgcaag     300
tgacccaatt ctaaatggtc tttttatgtt ttcaagccaa gctccgagca gcaaggttgg     360
tggtccaagt tcagacccta accaaaacag ctacccgagg ggctctatcg atcggaatgg     420
acacactcat tcgtagacgc agaaggtctc gttgtcatct tcgctttcct attctacttc     480
tgctactttc attgatcgga agggttatcg gagtcgtact tggattgttg atcaccagaa     540
tgttgatgag aaggcaataa tctacatacc ataggttgga aattgtatta g              591
```

```
<210> SEQ ID NO 7
<211> LENGTH: 501
<212> TYPE: DNA
<213> ORGANISM: Gossypium hirsutum

<400> SEQUENCE: 7
agatgctatt tggacatatg gtgactttac taaaagatta tcatcaggtc agcttcttct      60
tcttcttcat ttatcttaaa tgtggcaaat ggtttatatg ctgaataatc gagcatgttt     120
ctaataattg taactgacca ggaattccct aaaataaaca aggtgattac atgtgtccct     180
ggaagtgaga tcccggaatg gtttgatttc aaaagctcag gatcttccat aaacatccaa     240
ttgccttcaa agtggtacta caatagcagc aaaaactttc caactttcgt tgtttccact     300
gttgtttctt ccaagactat tctggcgac agagaaattc tcattagatg taaatgtcgt     360
ctaaaatccc gtaatggcga ctgtcatgac cttagttgtt cttttcttaac ttggacaaaa     420 cgaattcctg gaagcgaatt gactggatcg aatcacttgt tcctcttata taaaacttgt     480
ttctgtgatg aggatgatga g                                              501
```

```
<210> SEQ ID NO 8
<211> LENGTH: 673
<212> TYPE: DNA
<213> ORGANISM: Gossypium hirsutum

<400> SEQUENCE: 8
catcttctgc aatgatgata gtcaactttg gtactcgatt caggtgctac aaaccacatc      60
accaatgatg tctcgacact cagtcatctt actgaataaa caggtatgag ccaacttttg     120
atcggcaatg gtgctcctgt tcctattgat catgtaggga gatcctctat tggtacttgt     180
agtaggatat tacatcttaa acatgttttt acatgttccc tatgtctgta aaaatttgat     240
ttctgtagca cagtttactt gtttttttgaa tttcatccct ctcgttgttt tgtgaaggac     300
atcaagacag ggaaggtttt gctagtaggt cacattcata aagggttata tcgatttaac     360
acatcaccac aacaaagaag ttttgctggc tttgatgagg gctttcaata tgcacatact     420
actaagattc aagcttgaga caccttctgt tctgagttcg acttatggca caaaaggctt     480
ggccatccct gcacaaaaat tcttttttcaa gttcttcgaa gttgtaatat ttcactgaat     540
aaattcacac cacctagagt gtgtgttcct cgtcagctag gaaagtctca taagctggtg     600
tttgataatt ctaagactgt atatacttcc ccttttcaac ttgttgtgtc tgatttgtgg     660
ggacaatcac cta                                                       673
```

```
<210> SEQ ID NO 9
<211> LENGTH: 748
<212> TYPE: DNA
<213> ORGANISM: Gossypium hirsutum
<220> FEATURE:
<221> NAME/KEY: n = a, t, c, or g
<222> LOCATION: (1)..(748)
<223> OTHER INFORMATION: n = a, t, c, or g

<400> SEQUENCE: 9
aaagaggaga aaagagcctc ggccttctcc ttgcgtcgat tctaacgatg ggaaagaata      60
tcccggcgac gcaaccccg ggtttgggta agttttcctt cttctccctt ttatttattt     120
tgttgaaaaa taaatttaaa agagcagaaa aataaataaa aagaaaacc gaaagaaaaa     180 agagaaccca aaaatgagat ttaaaatcaa cttttatttt ttttgctttt tacttctgaa     240
aaaatttgcc tgtaatacaa ttttttttg tataccgaaa tcccctctta cattcggttc     300
ttccctcggc ttatatagcc gaatacatag aaaatatttt ctgctctctt ctattgtttg     360
ttgtttttcg ctctctttcc ttctgctttg tgtgcttctc ctttgttttg caggtaacgt     420
cagagtaggt gagcagaggc gatgggacgg gcgtctgttc gggcgcaaaa tgcgctgaca     480
ccacgtgggg gagggaggta cagcgcctag cataggaacc ctagggtttt ttcttttttt     540
ctgataaatt tgggctttgg gttaggttta gttgggcttt ggattgggtc atagttcggg     600
ctttgtattt gggctgtgaa ttgtaaaagg tatgggttga gcctgttttg tttgttcatt     660
gggcccggtc taatttgggc atttacaata tgtatgatgc aaatttcctg annnnnatnn     720
nnntagannn tagtatgcaa nnnnngct                                        748

<210> SEQ ID NO 10
<211> LENGTH: 615
<212> TYPE: DNA
<213> ORGANISM: Gossypium hirsutum

<400> SEQUENCE: 10
tttgaaaaat ttatgcaac tgctccacct acaaaataga aagcagatct caatcatttc      60
atttttgcag caaatatgta ttttaagggt cttaaagcca tgttatatgc atggacatgt     120
cattactcag tttatttgca caaatatgta tatatgtttt ggcttagaac tctaaaattc     180
tacatgcttt gtaggaaatc tttcatttaa atgataaaaa cacacctcag ttcttcctgg     240
cataataggc tttccagcat ataactcagc aagtatgcaa cctgtactcc atagatccac     300
agcggtacca tagtaagtgg ctccaagtaa aagttctggt ggtctatacc aaagggttac     360
gacacggctt gtcatgggtt gactttgatg gggatcataa aagctagcca gaccaaagtc     420
tgcaatcttc aagatgccat tattgtcgat tagaaggttt gaacccttta tgtcacgatg     480
taggacacca cggctgtgac aatgatcaag accacacaaa agttgttgta tgtaacactt     540
cacctgcaca atagatcaat aaattaaacg tcaggataac ctttcaatgg aaagtgcaaa     600
attctgtatt tgcag                                                      615

<210> SEQ ID NO 11
<211> LENGTH: 635
<212> TYPE: DNA
<213> ORGANISM: Gossypium hirsutum

<400> SEQUENCE: 11
gttactagct gtttagctaa tggattgctt gaagccgttg tgaagaaaag gtaactgagg      60
aggctcaaag agcaatggtt atggcttttt cttcccctg cattggactt agtactatgc     120
```

```
atatgcttta agcatgagtt tagaaaaggt gaatatccaa cttgatattt aatgaatctg    180
ctacttttgg aatcaatgaa atagatttgt cttattttttg aaatcaaata gttggtatta    240
tatttttttt tgttgaaata taaaacaaaa aattacataa acttattcat aaacagaatg    300
cctctagtac tgtctccttg tagagcttct ttaattgcct ctagaaattc ttcgaacata    360
tgcaaatagt cgtcatcatc tgttcgagct actgccttat taaattctct agggacatat    420
ttcaagaact actttttttc atttgataaa atctattaaa ttcgtctaac cagagtggaa    480
tttaatcttt caattttact gtcttcaata atttttacaa cctcaaaatt attttttttgg    540 ataacgaact catcataatc ttgttttatta atcaattaaa ccatccaaaa tgtcccaaaa    600
ttcctcaagg aatacaggac acttcccaaa aaaaa                              635
```

<210> SEQ ID NO 12
<211> LENGTH: 598
<212> TYPE: DNA
<213> ORGANISM: Gossypium hirsutum

<400> SEQUENCE: 12

```
tgggaacaat cgtaagagga tggcatcctt agtaacgcca ttgatcttga aagtgtcgca     60
aatctctaga aagttatcca aatgggcatt caaatcttta tcttgcaacc catcaaactt    120
aacatattat tgtatcattt gaattgtgtt cagatttagc taaaaattgt ttacagcaac    180
agtcgatctg acgatactcg attcagcccc aattcaagtg tgcttagcat aatcatacat    240
agtacgaaga gcaggagttg caagaagcag ttgattattt tgattaccac tcatctccat    300
ggtaatatca ttttttttttct tgatcatcta ctatatttgt tgattttgcc ttacttctct    360
aaccttttta tgattttttgc gagcaatctt ttcaacttca ctataaaaaa ttaatgattc    420
caacgagttt cctctagtca taaaccaaaa gaacctgtca gaatcaaacg aatgaacaaa    480
tttagaatgt aaaaattaaa ttaaaaacaa aaatattaaa attaaaaaat agctaaatta    540
atagaaataa aattttccta atattttagt ccctgtcaat agtggcaaac acttaatg     598
```

<210> SEQ ID NO 13
<211> LENGTH: 585
<212> TYPE: DNA
<213> ORGANISM: Gossypium hirsutum
<220> FEATURE:
<221> NAME/KEY: n = a, t, c, or g
<222> LOCATION: (1)..(585)
<223> OTHER INFORMATION: n = a, t, c, or g

<400> SEQUENCE: 13

```
gcgccgatct acgtctatca gcagagacga acagccccgg gcttcaaagg atgaccattt     60
cagtcgtggg atcccttcta aaccccgatt tcgacgaaat gaaggggata cgacggccaa    120
ctcgcaaggt aaacctctct tttgctttct ttttttgttt ttgagataga tttcaaaata    180
aaaagaaaat agaggcgtaa aaatgaaaac agggaacaac ctttgcagaa tattcaactt    240 ctttgtatttt gattcctctt ttttttgtgt aatctgttcg tagtcgtatt acaatcgaaa    300
atcaaaggct tnatagccga ataactaaag aaaacaacaa ttttttgtcct ctgcttttgt    360 attggcttgt tgctgctttc gtttgttttc ttttgcaggt acggagcacg gggctgtgcg    420
ttggcgctcg ggtacgggtc taggctaggg tacgaggtg gtacggtcgt tgcgaggctg    480
ttgcggcgca agagggtgac ctagggttcc cgaaagtgtt gaagttttttg ggcttnttgg    540 gctattcggg attgggctta ttgggctagg atattaagtt tggtt                   585
```

<210> SEQ ID NO 14
<211> LENGTH: 530
<212> TYPE: DNA
<213> ORGANISM: Gossypium hirsutum

<400> SEQUENCE: 14

```
gatagcttgg aaggatctct ctcttatatg taagagcaga gaactttgga ttatataaat      60
attaaaatag taaaaattta tattatattt taattattac tttttcataa tcatgctaat     120
ctataattct taagtgcata aaacacaaac cgtccgacac attaattaaa gtaggctcca     180
ctttgtcaac tctcaccttc ttgattcctt ttgggaaaag catcactgct catctatgac     240
ctcatgcgtt attattggaa aaagaaaaag tgggaaatgc atagagaaat tgcttagaaa     300
cctttgctgt tccctggaaa tttgagctgt ttttctttct tgttgcttat atacttattg     360
tttctcgttt ctttctgggg tattaggtgg tttgttttct ggttttgaac accaaactga     420
gataccttt ttcttgtcgt acgttgtcat gttgtcgtta ccttcaactt cctcatctat     480
ttctaaaatg aaatattgta gagctgttat ccaccgtaga cattctagac                530
```

<210> SEQ ID NO 15
<211> LENGTH: 699
<212> TYPE: DNA
<213> ORGANISM: Gossypium hirsutum
<220> FEATURE:
<221> NAME/KEY: n = a, t, c, or g
<222> LOCATION: (1)..(699)
<223> OTHER INFORMATION: n = a, t, c, or g

<400> SEQUENCE: 15

```
ctaatcactt acctacctcc attaattaca ttgaaacttg ataacctata ctagcacaat      60
ttgtaaagct gatttatcag ctcaaatgtc aacaaaatta catcaagtac attaccaacc     120
tagttctaaa caaaccaagt tacaaaatgt taatttaaag taacaaaatt agcagcattg     180
tcttcaactg cgacctgcat ggctcgggca gcttgttctt cttcttggct gcttcatgtg     240
ctgcatgaag gccaacttca acactcctct ttggcctgca tactgcatac ttccagctta     300
gctcgcaaat ccataaacct tgacacacaa agaggctttg tcaagatgta agcaagttga     360
tcctctaaac tgcaatgaat cagtttcact tcttgtgctt gtttcatttc tctaacaaaa     420
tgaagcttaa tgttgaagtg atttgtcctt ccatggaata ctggattctt tgcaattgca     480
acatcagatt ggttgtcaca cataatctct gttgcttccc tttagtgaag attcaaatca     540
gctaagattt tccttagcca antggcttgg ttgacaactc ctgcagctgc cacatattct     600
gcctctactg tcgattgagn aanaacaaat tgctcctttt cactcnaaca aaaaatngat     660
gaaccaagag taaaaacata tcctgaggta ctcttcatg                             699
```

<210> SEQ ID NO 16
<211> LENGTH: 560
<212> TYPE: DNA
<213> ORGANISM: Gossypium hirsutum
<220> FEATURE:
<221> NAME/KEY: n = a, t, c, or g
<222> LOCATION: (1)..(560)
<223> OTHER INFORMATION: n = a, t, c, or g

<400> SEQUENCE: 16

```
ctggctgttg gcctccagcg ttggtggccg ccgtatatgg tggtcggagt aatacgaaaa      60
gaggtctttt tgaccgtttg gttctcccca accctgattt aaaacctaaa attctagaaa     120
aagccttta aaagtaaaan aaaacaaaca aacccttggt tcccctctcc gatctcagaa     180
```

```
aggtaacttt ttttctttga atatctatat atgcatgttc tttattcgaa aataaacttg      240
caaaggaaat aaaagaacag aacgaaagac caccttgatt ctttttttat ccgattgcta      300
ttttttttgt gtctccttct aaaaaaatta caatgaaaaa tgtttatggc tttgtagccg      360
agtgattaca gttttttttt gttcttttt gctgctattt cttgctgttg tgtggccttt       420
tcttgtaggt ataaggctgg atgcaagtgt ggcatgctag tacgcggacg tggaggccgt      480
tcggaggttg cgctgtaggc tgggggctgc gacgcgccta acaaaccct agggtttctt       540 atttttaat tttcgggcca                                                   560
```

```
<210> SEQ ID NO 17
<211> LENGTH: 738
<212> TYPE: DNA
<213> ORGANISM: Gossypium hirsutum
<220> FEATURE:
<221> NAME/KEY: n = a, t, c, or g
<222> LOCATION: (1)..(738)
<223> OTHER INFORMATION: n = a, t, c, or g

<400> SEQUENCE: 17
tatattcccg aaatctcttt tactttcnca gtaaaccttt aaaaaaccga aatttacaaa       60
tcaaaactct gaacaaaatt acttaaatgc taagaaaatg agccaaaaac aaccggagag      120
gccccaagag ccaatcaatt acggagatat cttctccgga aaaggcgagc ttgccgagaa      180
gacagtggca cctaaagatg ttgccatgat gcagaaggcg gggaactccg tgattggtca      240
aacccagaag ggtggtgtcg atgcatctat gcaatttgca acgtcgaaga atgagagttc      300
gggattggtt ggccgcgaaa gagtcagtgc tgattctggt gtttatatta agagaccga      360 gtcccctaga aaacgtgtaa tctcggagta ctttggtaaa gaggtaagag gagcaatcta      420
tagagagagc tctaatttaa tatttgttac cgcttttta ttatagttaa tatatcaaaa       480
aattattctn atattataga aatgtctgtt tgaattaggt tgagctgagc ctaagtactg      540
agtctatact tagtaccaag tattaattta tttatgtttg tcaaaattcg atctaattca      600
acatataaat tttaaatttt actcaaattt actataatat ttatatgact aacttaaata      660
tgtttacatc atccattttt taaaatttaa tttatctttt tttattaatt tttaaacata      720
aacaacatta aaatattt                                                    738
```

```
<210> SEQ ID NO 18
<211> LENGTH: 557
<212> TYPE: DNA
<213> ORGANISM: Gossypium hirsutum

<400> SEQUENCE: 18
aaacacgaaa ggttgttgat ttgttttatt cctttctttg aaactacgca tatattcata       60
catatttcat ttttatttgt gttctatgta tatatataag atatattaat aagttttttt      120
taaaaaaaag aaaaaagcga aaaaactaaa attttaccct ttttcgaaaa tccggccacc      180
gtgtacggtg gtcggcggcg gtggcgcatg gcggtgctgg agtctcaccg gaaatcccca      240
ggctgagaga gagagagaga gagagagctt ttttgaagag aaagaaagaa aaaatgaatt      300 ttttacaaa tttttttgct tttataacaa tatgaaatga cgccgttttg cattaaagac      360
ccagggcata aaatgacgtc gttttgtcct gggtcggatt gacctgaccc atactcgctt      420
agaatccgcg tgttttgac ggaagggcta attgcacttg tagcccttcc gcttttttat       480
agctttgtaa tttaatttt tgtatttta attttgccca aaaattttat ttttgtttca       540
ttttggtcct ctgctgc                                                     557
```

<210> SEQ ID NO 19
<211> LENGTH: 450
<212> TYPE: DNA
<213> ORGANISM: Gossypium hirsutum

<400> SEQUENCE: 19

```
cgctgctcta attgtgtcca gctcaaccac aacaatatga tttgagctgt caccgttgtt      60
tgattgattg aaaagaccaa gatactggct gggaagagct ccaggaattc tattattagg     120
cgagattaaa aaggctaatc catggccaga caaagtaggg tattcctccg gtacaattgc     180
aaaaaagaat gtggtcgaaa aagagaaaac actaccattt gtggagttct tgaattggat     240
tggattcttg tagaagatgt gacctgttga ttggattgta gaattagtca gttttaagag     300
cccacttgaa tctacgcctg caactccatc aacattcaag taaccattga aactgaactg     360
accctgattg atatctgaag atgcaaggtt caggaggaaa agcaacacaa gcatgatcaa     420
gcaagacatc attacacaca caaaaaaaaa                                       450
```

<210> SEQ ID NO 20
<211> LENGTH: 548
<212> TYPE: DNA
<213> ORGANISM: Gossypium hirsutum

<400> SEQUENCE: 20

```
tgcgtgataa attatatcca ttttccttga agataaaata tggtggctgt gaaaccaata      60
atttacggac aacagattgc ttagatcata acgtgatgg gcttcatgtg tatttcaatg     120
ggcatagcct taaggtgaag aagtgtggtg ttagaatagt gtatgagaaa gatttggaag     180
aaataaaaga gttgcagtgc catacccctc aatcttcacc aaattttgaa cacatccacc     240
aacactctgc tcacaacgat ggatcagtag gtagcacttc tgacattaaa caagaacgta     300
atatctccga ggaagcggag gaagaggggc agcaaccaaa actgttgcaa aaattttca     360
atttttataat gggccaatca gggaagaagc attaactgtg gtaaactact taaccaatct     420
tgtcctatta actttttttc acatctttca tttaatgtga tcaatctaga cttacttacg     480
atccttctta cataccacaa agttataaat cttttactca tattcaacag gagctcatat     540
tccgtaaa                                                              548
```

<210> SEQ ID NO 21
<211> LENGTH: 415
<212> TYPE: DNA
<213> ORGANISM: Gossypium hirsutum

<400> SEQUENCE: 21

```
gcccttgatt cggtttgtat tatcttctaa tccaatctat ttgctatctc cgaagtttgt      60
tgggagaaaa gcttgaccgt attatgcgaa cgttttggtg gggtcatgat ccgaatcaga     120
ggaaacttca ctttgggaaa ccgaaaacca atggtggact tagtattcac agcatggagt     180
gatgcattac ttagtaagca ggcctggagg ttactgactg aaccccaaca cttcgccata     240
taggaaaata tcatcgacac caacatttct ttaatggaag agtttagttg aaggagacga     300
gatggttgtt tgagtggtat tgatatctaa atttgcaagg tgcaaacaac tcttttaag     360
tgactaggtg atggatgatg ggtagacaaa ctttctaacc cacgcttctc acact         415
```

<210> SEQ ID NO 22
<211> LENGTH: 646
<212> TYPE: DNA

<213> ORGANISM: Gossypium hirsutum

<400> SEQUENCE: 22

| | | | | | |
|---|---|---|---|---|---|
| ttctggagcc | ttctctggat | attccctcca | ggtacttctt | taaataaggt | tatttgtttt | 60 |
| ggaagtgctt | gaaaaaacaa | tatttcaaat | taggctgatt | aggtataacc | aataatgtta | 120 |
| ttacttgtaa | acaattgagg | ctgcaaaata | caactgtttg | aagcaatatc | aagaagccgg | 180 |
| tttgatacat | tgtgaagaaa | taacacgact | tggagcagtt | aagttttgga | tcttgcattt | 240 |
| gtggatggac | ttatccatta | gtgtttacat | accataggga | atttgtttgt | aacaagtttt | 300 |
| cttgggcttg | tgtttacagt | tgcttatctt | ggtctttgga | tatgatagtc | ctttgggatg | 360 |
| cctcctttc | ttaaatatta | tttataataa | gttttcttag | gcaccatctt | tagtgttttg | 420 |
| tcatattggt | tgcatattgc | taatcttcat | taatcttgat | taggtgatgg | agtcccatca | 480 |
| agcaggcaaa | ttggacactt | ctggtactgc | taaggctatt | atttcttgct | ttcagaaatt | 540 |
| gggggtgtca | tttgacatgg | atcaggtgtg | tggctcttac | atattcttaa | ttgtaattga | 600 |
| aagagaaatc | aagttctttt | ttcttattgg | ttaggggctg | gggagg | | 646 |

<210> SEQ ID NO 23
<211> LENGTH: 645
<212> TYPE: DNA
<213> ORGANISM: Gossypium hirsutum

<400> SEQUENCE: 23

| | | | | | |
|---|---|---|---|---|---|
| taacattttg | attgctctaa | ctttaaaaaa | ttctaaaata | ctcattaaat | tatttcaaaa | 60 |
| tttttatttt | tatttcaaaa | agaaaagcat | aatgccttgt | tgtttaacaa | taatgccaaa | 120 |
| atctaattag | catgcagtag | aagtagaggt | gtttaggttg | gagtctagct | caattaaaat | 180 |
| tttaggaatg | tttgttaagt | ttggatttga | ctttacctta | aaaattgatc | taaaattttg | 240 |
| gtcaagctcg | atgtaaataa | aaatattaaa | atttcaagtt | cggccggccc | atattcaaat | 300 |
| tttttatata | atatttttat | aaaaataata | taatacataa | aaaatactaa | aaacattaaa | 360 |
| ataaatgtct | cccagcaatt | tgaaaataaa | ttttaaaaat | atatgtgctt | aaataacact | 420 |
| gagataagtg | caatttaaca | gacaaatacc | tttaaaatag | taacaaaatt | aacaataaaa | 480 |
| taagaattat | ataatatcca | aacaataaga | acaatatagt | aacaaaataa | tagtaaaatg | 540 |
| atagcaaaat | agtgagaaaa | caataatata | gcagcaaaac | aataaaaaac | aacaagaaaa | 600 |
| caacattttt | tttattttg | tagattcata | cgagctgagc | ttcag | | 645 |

<210> SEQ ID NO 24
<211> LENGTH: 611
<212> TYPE: DNA
<213> ORGANISM: Gossypium hirsutum

<400> SEQUENCE: 24

| | | | | | |
|---|---|---|---|---|---|
| tcatgttaga | gggtacacac | ctggtatgat | tttgatgtga | aaccacacca | gagaccacca | 60 |
| gcacctaaaa | gaatacccaa | caccttttta | gcaatcaaat | tgcaaatcca | tcaatactaa | 120 |
| accgaacagc | gtacacatac | ttaccactat | caaacccgat | cacgcgcaca | gattagactg | 180 |
| attgagcgaa | aactgcagtc | tcaactcctt | ctcctgcaca | aaacgtttac | agagaattat | 240 |
| tttcccttac | aacttacact | aagaattcaa | gtgaaaagga | gaaacccat | agcttactga | 300 |
| agatgaaacc | tatcgacaag | tgaaagcccc | cacttatctg | atcacacgaa | aaacactgaa | 360 |
| atcccaaatt | gcatgtgaag | aacaaaagga | gagtacagat | tgaaaggga | aaattgaaag | 420 |
| aagaagagaa | tagtggagaa | aagcaaaaac | gtacgtcaga | aatttggaa | gagagagaaa | 480 |

```
cgaaattaga aaaaaataaa ataaaataaa caacaatatc tatcctaacc tctcattctt      540
tcccactcga actagtaagt ttattttaat atgagttaat aaagaatatt acataagcct      600
acccagtaga g                                                           611
```

\<210\> SEQ ID NO 25
\<211\> LENGTH: 300
\<212\> TYPE: DNA
\<213\> ORGANISM: Gossypium hirsutum

\<400\> SEQUENCE: 25

```
aagtttagtc aacttctaaa ccataaagaa cattagcata cttttcaatt gggtccccat       60
ctgcaaaata cctttccttt atcttcaacc aagcgtgcaa tgtcaacaaa ctatcggaac      120
cagcttgatg actcttccca attgcacgct ttactcccaa atctgtagac gcacgatcga      180
gacctccatg taatccagcg cagaatttca tcaagtgttt gacgtcgtag attctgtctc      240
cgaagaacac tcgcacgagt tccaaaaact cagtgagttg gtcaggcaat aacccaccgg      300
```

\<210\> SEQ ID NO 26
\<211\> LENGTH: 631
\<212\> TYPE: DNA
\<213\> ORGANISM: Gossypium hirsutum

\<400\> SEQUENCE: 26

```
atgttaattg ccataggctc aaaatgtgct ttgcatgctg ggtttcccat aacattgcac       60
tgagttatga attttttatg ctaattgca tgttaaggat tgatgaaatt ttgtacaaaa      120
tattaaatca aacagataa aaacctttct atctgtaatg catgttttca tctgcacagc      180
aggcatgtgc acagatcaca aaccatcaca acataaacct ttggtttgct attatctatg      240
catttcccga ctgttcattt ttcttgaagt atttgtcttg cgattatgaa tatatgaccc      300
ttcaatacat ggaaaaactt agaaaacaat taaacatacc cgtatctgaa actcgcccaa      360
atccaagtaa catgggctcg aatatctctt attatattgg ttacttcccg ttggtcttcg      420
taactctttc aagatatgct tttacttatg agattatgtt gttttagttg ctttttcttag      480 attttgatcc aacattaaat ggatgtttta tgtgttcaa gggtgctttt tgagaaactg      540
aatttaaatt acgaggaggg tgagagatgg attgtgaatc tcatccgaaa ctctaaactt      600
gatgcaaaga ttgattcaaa gactggaacc g                                     631
```

\<210\> SEQ ID NO 27
\<211\> LENGTH: 658
\<212\> TYPE: DNA
\<213\> ORGANISM: Gossypium hirsutum

\<400\> SEQUENCE: 27

```
ccgatgggaa agccactgga gaggcatacg tggagtttgc ttccgtcgag gaagctaaaa       60
gagcaatgtg caaggataag atgatgatag ggtctcgata tgtggagttg tttccttcaa      120
caccagacga agctcgacga gccgaatcaa gatcgaggca gtgaagaggt cctgttatct      180 gggttttga tatgtagtct ttggtttgta tgtttgtcat tctagcctga agaaatgcat      240
gtcaacccat atttaatggg ttaatcttct tcctatgtgt gtctctgctc tcaaaatata      300
atctcctaat cctattaggt taaatatgat cagtatgttg ttgatgtact ttttttttgtt      360 tttcttttag atatttgaat tttggttta aggatataaa atatatttta gataaatatg      420
tagacttttt acctttcaaa ttcatgctca tggttgcctt cgggtggttt cattgttcat      480
```

```
tttgcatgtt gtggtattgc catggcatta aatagagtcc ttcttgatcg aagattttaa      540
agattattat ttgttacatt gggtggtttt aattccacaa ggttatttat tttttaaata      600
ctagttaagg ataaaaaaat ccaaagggcc gatggattgg gtttcaatcg gattaaaa       658
```

<210> SEQ ID NO 28
<211> LENGTH: 578
<212> TYPE: DNA
<213> ORGANISM: Gossypium hirsutum

<400> SEQUENCE: 28

```
gaaaaattat ataaaaattt gtgtcggtat tatcttcact tgacccttgc tttaccattt       60
tgattcgccg aacaatccaa gaatttaaca cccacaaggc cagaacaatc gcctatcacc      120
gccgtagccg acacccaaaa tgaggaagga agcggcgccc tcctccgtcc cttccgccgc      180
cgcaggcacc accactttgg ggaagctatt catttgcttc gagaccaaaa cattagtgac      240
cacattgctg gcacttactt tagttacgtt cttatggaac ttacctcctt actaccaaaa      300
cctcctctcc accaccgtc cttgctccgc tccgataacc tccgtttccg tcaccgcttc       360
cgccgcatcc gtcaccgcca gtttgatctc caccaatgtc tcaatgcctt acaagccgaa      420
tccggtagct aagaagtaca acacggcgac accacctaaa cccaaggacc caaacaagcg      480
ggttttcgag tcgtacggga acgcggcggc tttgtttgta cagatgggtg cttacagagg      540
aggaccgagg acgttcgcgg tggtgggatt agcttcca                              578
```

<210> SEQ ID NO 29
<211> LENGTH: 652
<212> TYPE: DNA
<213> ORGANISM: Gossypium hirsutum

<400> SEQUENCE: 29

```
atgaatgctg acgacttgct cgatgatttc tctaccgaaa ctttgcggaa agatctaatg       60
gctgggaaca agctgatgaa agaggtacgc ctttttcttt caagctcaaa tcactttgct      120
tacggtctca aaatgggtca gaaaattaag gccattaagg cgaggttagc ttcaattgaa      180
agtgaggcca cacttttggg ctgcatggtg cgtgaccgcc cagtggaaac ctcttttcatg     240 attaaaaaga gacagcgaac acactctttt gtgagtaaag ataaaataat agggagggat     300
gatgataaag cggctctttt aaaactcatg ttagagtttg aaagtgaaga gaacgtttac      360
atcattccag ttgtggagtt tggaaggtta gggaagactg cattggcgca gtttgtttat      420
aatgataaaa tggtctatga ttattttcaa ttgaggatgt gggtgtgtgt ttcagatgtt      480
tttgatgtca aattaatttt agaaaacatt attaaatcta taactggcca agtaccagat      540
caaaatctcg aaattgacca attgcaaaaa caacttcgag ataaaattgg tggaaaaaaa      600
tatttgcttg ttttggatga catttagaat gaagagaggg aagaatgcgt ta              652
```

<210> SEQ ID NO 30
<211> LENGTH: 579
<212> TYPE: DNA
<213> ORGANISM: Gossypium hirsutum

<400> SEQUENCE: 30

```
tgcatcacag aacattgaat tttagggttg agagaagaaa gagtaaaaac caacaacgat       60
tcctcaaccc atgtctttgc cttcgcctcc tatcgccatt ctctctacac ctttaagtcg      120
cactttcagg agggagagat ctgtcattgt ttggcatccg gagagtgttt tcttccactt      180
tctgagacgt gcattatatt actacagtag tcttgatcgt gaaattcagg taagttcttg      240
```

```
gtattgtttt gttgagtcta atttgttatg gttttcgttg atcgaatcag ttatagacca    300
tcagatttgg gattcaacaa agtacaagta ggacgtgcgc aatggacatt gacacggagt    360
ttgagggtct gaatttgttg tttaagtctt aaactagtaa tggattttcc ttttgcctga    420
gttctttgtt aacttaatta ttgtaaaatt gatgtaaact tatatgagaa gttgctgctg    480
ttagctcttt ccataagcat tttccataag catcggaagc ttaaaaggtt acttttaacc    540
tgtttatcat cttttctttt ggactgtaat tgtatgata                           579

<210> SEQ ID NO 31
<211> LENGTH: 585
<212> TYPE: DNA
<213> ORGANISM: Gossypium hirsutum

<400> SEQUENCE: 31
tacctcccag ttacaaaagt cccaactttc catctcaacc gtccatcaat cttgatcatc     60
aaaaaaacac tcccggccat ctattcagca cccaatgcga cggaatattc cggtgagatc    120
ggtaccatag taccatatat tataggtgac caaatattga cctcaatatg gccttgtcca    180
gagtgttatt tcttggttcc cgttagaagc gtaaacgtcg agccggtcgt aataaacacc    240
gatatcgtcg tttgggttac gtgaacggac tgtgatttga agtttgaag tgagggagtt     300 gacggtggtg gcgttgaagg cgtagacggt ggtgtcgagg agagtgaagt tggatttgct    360
gggaggaagg attgcccata tgagtaagat tgtgatgaga atgaggagga ttagaataca    420
agcgatgact cggcgaaaaa atttctggcg ggatttgtgg tggtggccgc cgcagtctta    480
gctaccagac atggtggatt tggaagttat tgggtttctt tttggtgatt gtgtgaggat    540
ttagtgatgg aatagtattc agtgtgtgct attagctttc ttgtg                    585

<210> SEQ ID NO 32
<211> LENGTH: 592
<212> TYPE: DNA
<213> ORGANISM: Gossypium hirsutum

<400> SEQUENCE: 32
acagaaatag aaatgattgc agtctgtcta ttttctttcc ttttattgga attaaatatt     60 gatgttttt ctcgaaataa agaaatttat gcatgtcata tgggctttga tatcttctca    120
ttgttgagaa cttggttctg aaatggttac tatgttctaa ttgtttttttt tttctgattt    180 ttagggaaaa cacgggcaag agatgctgcg ctaaatgcta tccagtcgcc tttgttagat    240
cttggtatag aaagggctac tggaattgtt tggaacataa ctggtggaag tcatttaacc    300
ttgtttaagg taacgcgcca tctccgactc tctcagtgtg tctgcgtttt cttgcggaga    360
ctttatatat tatcttgata ttgagcgcaa aattgttgat tattcgtaaa tggagcactt    420
ccctgtagga gaagagtcat tgaagcccaa gcggccccac catatctgat acctgcattc    480
ttgagtaaca gacaagtgaa taattggaaa tagtatagta atgaatacta ctttgtcatt    540
gaaatgttat acatgggaaa ccttgattat attgactgat ccacttgggt tc            592

<210> SEQ ID NO 33
<211> LENGTH: 620
<212> TYPE: DNA
<213> ORGANISM: Gossypium hirsutum

<400> SEQUENCE: 33
tcaaagttcc atccaacata gaagttcaag cctgaaagtt ccaccattaa cgatttcttc     60
```

```
ttgtcaaccc catcttcaac atcctgcaaa tgcatctgtt ccattgagct caattctatg    120
ttggaagcac cattggctac tggacttcca ttaatttcaa gtccagacgt gtctacactt    180
ccactcaatg tctccatccc aacactgtta ttttctcaat tttccaacct tgtctaaag     240 caaatttacc ctcctgtttg aaaactgacg atcttcatcg gttgattggg cttttgaaaa    300
atatatcttt ttcttttttg gtacctttca aagtccattc aagcagcaaa gcaaacaagc    360
aacttattca cagatattgg atcattacgc atgataacgg gatttattag tgttcatcgg    420
attgatcatt tagcccaata gactttgagc ctaaacccaa gatctgtcct gaattaaaag    480
aaataaaaat tggatttcaa tttccaaaat taaaaaacaa ctgaaattat aacatcaaat    540
ttgcattact gccaccaagg caccaatcaa gatttgaacc cttcttcttt tgacatggag    600
aaggatgact gttgcagtta                                                620

<210> SEQ ID NO 34
<211> LENGTH: 574
<212> TYPE: DNA
<213> ORGANISM: Gossypium hirsutum

<400> SEQUENCE: 34
ctttactatt cgcggtggct gcctcttttc ttctctacac gtgagcagta ctgaaatttg     60
cagactttct tttcttcatt tcctagtcgt ttcgagtttc tttagtttat aattttctat    120
cagttgtttg aagaaaacat ttcggtgttg ttgatttgct tgctctttat gtttttatt     180 tgattattaa cgactcatc atctgatctg agttaaaatt ttcagatctg tacagttttt    240
tttgaatagt ctccaagcaa ctatgggcca tcaacagctt gcgagggagg catcttaagc    300
acaatatgac taaacgaacc tccattgttg gcaggaagca agaaaagaag tcgggagaga    360
gttttcgatc ggttcccttt agcttctcaa aacttatctg aaattctttc ccggcttctt    420
ttcttgcttt cgttttattg ttcgtttgcg ttgtgcttca gatgtcgcac atccaggctg    480
tttgaagttt tttgtaggcc aacctaatct ccatggaaga aatccagtag ccgaagttga    540
ggtgaagtgg agattgttcg aaaaaacact ataa                                574

<210> SEQ ID NO 35
<211> LENGTH: 789
<212> TYPE: DNA
<213> ORGANISM: Gossypium hirsutum
<220> FEATURE:
<221> NAME/KEY: n = a, t, c, or g
<222> LOCATION: (1)..(789)
<223> OTHER INFORMATION: n = a, t, c, or g

<400> SEQUENCE: 35
ttcttaaaca aaccctaaac cttaatttct ctcacatttt caatggaatt tnnngggtaa     60
attttccttt acatcttaca tttctttcag ttaaaatttg ttctttgaat atttgtttca    120
attgcgaaat tagttgaaat taataattat ttatgtttga ttatcgatta tttacgtttc    180
tttgaaaatg ctaatcgtat gttcagatgc tgtcttctag taaggatttg atgtttcagg    240
ctgtttcttt tgctaactat ttttcttta atatgatatt ttttatctt tgattttgta     300 tgtaagagtg cggcatggaa ttatatatat atatacatgt tctcccagat agattcattc    360
actcttttga attagaattt aggtttggta tttctattga ttttgttctt ttaaattgtt    420
ttcttagttt catttcacgt ctgattaaag gaaaattact tatgttgtac aattttttct    480
caagcatttc tctgtaaaat ttccctataa tttactcatt atgaatattg aagggaaaaa    540
aagaaaatga tacctttttt tccttgttaa atcgtaattt ctttggacat tattaagggt    600
```

```
ttgaaataat attttatagt ttgatgtttt gaattggatt accctgttgg aaaccttttta    660 gaatatgttc tatctgctac tactgttggt attgcgtttc atcatttggt gttattgtag    720
ttttttacat ctcaatgatg attgcttgtc aaatattttt tgattgttac atattttgcg    780
atttcatgt                                                             789

<210> SEQ ID NO 36
<211> LENGTH: 687
<212> TYPE: DNA
<213> ORGANISM: Gossypium hirsutum

<400> SEQUENCE: 36
taaggctggt caagacacat tgatttcagt atataatata catcattcct cacaggtgct     60
tgcttatttt catcatactc gtaattttt ttctttgaat ttttttcctgg ttattactcc   120 tatgttgttc cgtttcttca ttttcttaa aatgcctgtg tttgataccct tgtccgatg    180 tatataacct aaaagacccc gccaaatata tgggaatact tagaaaaaat tttgaaaata    240
tccaaatcct ctgtgaaata cctcattttc tgttgttcgc agcctacgta tcaaattgta   300
catgcactat ctctatgctg aatttgctga ctgcataacc gatcaacgtt tggtttcctt    360
caaatagaat attctaagtt tgaaaatagg gagttttacg attcctacca tttgttttct    420
tggacagcaa taagcgatat tccgtctttt tcttctttcc aggtctggga aagagctgaa    480
gagtttgtgc ccgagaggtt cgacttggaa agctcagtcc ctaaggaatc aaatacagat    540
tacaggtacg aaaaacaacc gtgttttact agttttctcc ctgtccctga tatccttccc    600
acatttgcat tacatactct tcatcatatt aatacggtag aacatcttca ggttcattcc    660
gttcagcggg ggtcctcgta aatgtgt                                        687

<210> SEQ ID NO 37
<211> LENGTH: 620
<212> TYPE: DNA
<213> ORGANISM: Gossypium hirsutum

<400> SEQUENCE: 37
tagtgagggt atggtgaaac gtcaggatgt atgggtcacc tcaaaactat ggtttgcttt     60
tgtgctttaa tacttttctt tataagttct tctcaatgga gtccgttact ttgcatatct   120
aatatgtcat tgcgttgtac gtttaggtgt actgatcact tgcctgaaga tgtaccaaag    180
gcattgcata aaactctgca ggatttgcaa cttgattatg ttgatctcta tctagtatgt    240
cttaacactt actttattga atgatatat atgtatatat gacatttgtg gtaactgcga    300
tgaatgttga agatacattg gccagtgagt gcaaaaggg gagcaattgc tgtgaagggt    360
gaaagcctta cacaaccaga catcccagct acatggaaag caatggaggc actctacgat    420
tccggtaagg ctaaagctat tggagtgagt aatttctcgg caaagaagct cagggatcta    480
ttggaagtgg cacgtatacc gcctgcagtc aatcaagtgg aacttcaccc tgtatggcag    540
cagccaaagc tgcatgaatt ttgtaaatcc aagggaattc acttgtcggt aagaaaacag    600
gccgcttcag gttcatatca                                                620

<210> SEQ ID NO 38
<211> LENGTH: 669
<212> TYPE: DNA
<213> ORGANISM: Gossypium hirsutum

<400> SEQUENCE: 38
```

-continued

```
gggtgactaa tgaagaacat aggaagggga ttttcccaat ataaaagaa acaatgtaa      60 tattgtggac caagtcaaat aaaaccccac aacatgtaac gtaatgcaca ctaccatcac   120
aaccaccact aaaggcacgt caaaccgccc ccaaagcaca cgtatacgcg caatagaacc   180
ggcgtttaaa gatgcatagc ctcggaagtg gtcgaccgat tccatgactc catcactatc   240 cttttacct tacctagtcc tcaccaaaat caatcattta aaagtataat aataatattc    300
tgatattaaa tgaaaaacgg ggatgttgta ataaaacctc gttcatttca ttaacatttt   360
cactttcaac aagatatatt tattcccaga ttaaaaaaga gtaacccctt cctatagctt   420
taactggttt tccctaagcc caagtaatg aacaaaatct ggctgcaacc ccatatatat    480
atatcatcat cattcctgga aactagaaaa ttattgattt tcatctaaac ctaaccctaa   540
aaacctatat atgtcttcta tactactaat atagtcaaca accatatgca aagttgagtc   600
aataagtcca atcttgtggt aactggactt cacggttgat cccttgctga ggccttgagt   660
tatgcttgt                                                          669
```

<210> SEQ ID NO 39
<211> LENGTH: 30
<212> TYPE: DNA
<213> ORGANISM: Artificial Sequence
<220> FEATURE:
<223> OTHER INFORMATION: Description of artificial sequence: synthetic
      primer

<400> SEQUENCE: 39
caaacaagca acttattcac agatattgga      30

<210> SEQ ID NO 40
<211> LENGTH: 25
<212> TYPE: DNA
<213> ORGANISM: Artificial Sequence
<220> FEATURE:
<223> OTHER INFORMATION: Description of artificial sequence: synthetic
      primer

<400> SEQUENCE: 40
cagatcttgg gtttaggctc aaagt      25

<210> SEQ ID NO 41
<211> LENGTH: 34
<212> TYPE: DNA
<213> ORGANISM: Artificial Sequence
<220> FEATURE:
<223> OTHER INFORMATION: Description of artificial sequence: synthetic
      primer

<400> SEQUENCE: 41
cctagtcctc accaaaatca atcatttaaa agta      34

<210> SEQ ID NO 42
<211> LENGTH: 32
<212> TYPE: DNA
<213> ORGANISM: Artificial Sequence
<220> FEATURE:
<223> OTHER INFORMATION: Description of artificial sequence: synthetic
      primer

<400> SEQUENCE: 42
aagtgaaaat gttaatgaaa tgaacgaggt tt      32

<210> SEQ ID NO 43
<211> LENGTH: 32

```
<212> TYPE: DNA
<213> ORGANISM: Artificial Sequence
<220> FEATURE:
<223> OTHER INFORMATION: Description of artificial sequence: synthetic
      primer

<400> SEQUENCE: 43
cttattcata aacagaatgc ctctagtact gt                                    32

<210> SEQ ID NO 44
<211> LENGTH: 27
<212> TYPE: DNA
<213> ORGANISM: Artificial Sequence
<220> FEATURE:
<223> OTHER INFORMATION: Description of artificial sequence: synthetic
      primer

<400> SEQUENCE: 44
tgatgacgac tatttgcata tgttcga                                          27

<210> SEQ ID NO 45
<211> LENGTH: 18
<212> TYPE: DNA
<213> ORGANISM: Artificial Sequence
<220> FEATURE:
<223> OTHER INFORMATION: Description of artificial sequence: synthetic
      probe

<400> SEQUENCE: 45
cgatgaacac taataaat                                                    18

<210> SEQ ID NO 46
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 46
atgaacacaa ataaat                                                      16

<210> SEQ ID NO 47
<211> LENGTH: 17
<212> TYPE: DNA
<213> ORGANISM: Artificial Sequence
<220> FEATURE:
<223> OTHER INFORMATION: Description of artificial sequence: synthetic
      probe

<400> SEQUENCE: 47
acaacattcc cgttttt                                                     17

<210> SEQ ID NO 48
<211> LENGTH: 15
<212> TYPE: DNA
<213> ORGANISM: Artificial Sequence
<220> FEATURE:
<223> OTHER INFORMATION: Description of artificial sequence: synthetic
      probe

<400> SEQUENCE: 48
aacatccccg ttttt                                                       15

<210> SEQ ID NO 49
<211> LENGTH: 18
<212> TYPE: DNA
```

<213> ORGANISM: Artificial Sequence
<220> FEATURE:
<223> OTHER INFORMATION: Description of artificial sequence: synthetic probe

<400> SEQUENCE: 49
ctccttgtag accttctt                                                    18

<210> SEQ ID NO 50
<211> LENGTH: 16
<212> TYPE: DNA
<213> ORGANISM: Artificial Sequence
<220> FEATURE:
<223> OTHER INFORMATION: Description of artificial sequence: synthetic probe

<400> SEQUENCE: 50
ccttgtagag cttctt                                                      16

<210> SEQ ID NO 51
<211> LENGTH: 17
<212> TYPE: DNA
<213> ORGANISM: Artificial Sequence
<220> FEATURE:
<223> OTHER INFORMATION: Description of artificial sequence: synthetic probe

<400> SEQUENCE: 51
tgataacggg atttatt                                                     17

<210> SEQ ID NO 52
<211> LENGTH: 17
<212> TYPE: DNA
<213> ORGANISM: Artificial Sequence
<220> FEATURE:
<223> OTHER INFORMATION: Description of artificial sequence: synthetic probe

<400> SEQUENCE: 52
gatcaatccg atgaaca                                                     17

<210> SEQ ID NO 53
<211> LENGTH: 17
<212> TYPE: DNA
<213> ORGANISM: Artificial Sequence
<220> FEATURE:
<223> OTHER INFORMATION: Description of artificial sequence: synthetic probe

<400> SEQUENCE: 53
attaaatgaa aaacggg                                                     17

<210> SEQ ID NO 54
<211> LENGTH: 17
<212> TYPE: DNA
<213> ORGANISM: Artificial Sequence
<220> FEATURE:
<223> OTHER INFORMATION: Description of artificial sequence: synthetic probe

<400> SEQUENCE: 54
gaggttttat tacaaca                                                     17

<210> SEQ ID NO 55
<211> LENGTH: 17
<212> TYPE: DNA
<213> ORGANISM: Artificial Sequence

```
<220> FEATURE:
<223> OTHER INFORMATION: Description of artificial sequence: synthetic
      probe

<400> SEQUENCE: 55
tactgtctcc ttgtaga                                                      17

<210> SEQ ID NO 56
<211> LENGTH: 17
<212> TYPE: DNA
<213> ORGANISM: Artificial Sequence
<220> FEATURE:
<223> OTHER INFORMATION: Description of artificial sequence: synthetic
      probe

<400> SEQUENCE: 56
tagaggcaat taaagaa                                                      17

<210> SEQ ID NO 57
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 57
tttattagtg ttcatc                                                       16

<210> SEQ ID NO 58
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 58
tttatttgtg ttcatc                                                       16

<210> SEQ ID NO 59
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 59
aacggggatg ttgtaa                                                       16

<210> SEQ ID NO 60
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 60
aacgggaatg ttgtaa                                                       16

<210> SEQ ID NO 61
<211> LENGTH: 16
<212> TYPE: DNA
<213> ORGANISM: Artificial Sequence
<220> FEATURE:
```

<223> OTHER INFORMATION: Description of artificial sequence: synthetic
      probe

<400> SEQUENCE: 61
tgtagagctt ctttaa                                                      16

<210> SEQ ID NO 62
<211> LENGTH: 16
<212> TYPE: DNA
<213> ORGANISM: Artificial Sequence
<220> FEATURE:
<223> OTHER INFORMATION: Description of artificial sequence: synthetic
      probe

<400> SEQUENCE: 62
tgtagacctt ctttaa                                                      16

<210> SEQ ID NO 63
<211> LENGTH: 658
<212> TYPE: DNA
<213> ORGANISM: Gossypium hirsutum
<220> FEATURE:
<221> NAME/KEY: n = a, t, c, or g
<222> LOCATION: (1)..(658)
<223> OTHER INFORMATION: n = a, t, c, or g

<400> SEQUENCE: 63
attgagtctt acaatcccaa acaaggacat aatcatgtaa acaaaccaca ctatgtcaat        60
actgatctct atctatgtcc acagccaagt cactactaaa tacttaacaa acctatgcaa       120
taacataaga tgacaattcg tactaagctt ataatgcata tttgggtcna ttacagncat       180
tgcgttttat gcntatattc agttgttgcc taaattgaag ttcatataaa gtcaagtcag       240
ttgcctagat ggataaacac aagcaatncg gatcaacaca taaacagaaa taatgtcata       300
ccaataggac attatagcag gctgatccac tatgctctca caaccaccaa atgatggagc       360
aatgtatggt atctttaatg catcaacaaa cttgatggtg gtcatcaaat ctccatccac       420
ctgaatgatt tagaatacat taatgtcaaa taattttgc atcaataata ccaaatgaag        480
taatagatac taaaggtgaa ttttccgagg tgcaaggttg aagtagttga agaaaacaaa       540
cctcaaaact gaccacacca ccaaagccag tcatttgctg cttggcaatt tcatgttcag       600
gatgacttgg caagcctgga taatagacgc gnctcacctg ccattgatat ttgataag        658

<210> SEQ ID NO 64
<211> LENGTH: 802
<212> TYPE: DNA
<213> ORGANISM: Gossypium hirsutum
<220> FEATURE:
<221> NAME/KEY: n = a, t, c, or g
<222> LOCATION: (1)..(802)
<223> OTHER INFORMATION: n = a, t, c, or g

<400> SEQUENCE: 64
atacattgct cntcatttgg tggttgtgag agcatagtgg atcagcctgc tataatgtcc        60
tattggtatg acattatttc tgtttatgtg ttgatccgaa ttgcttgtgt ttatccatct       120
aggcaactga cttgacttta tatgaacttc aatttaggca acaactgaat atatgcataa       180
aacgcaatgn ctgtaatnga cccaaatatg cattataagc ttagtacgaa ttgtcatctt       240
atgttattgc ataggtttgt taagtattta gtagtgactt ggctgtggac atagatagag       300
atcagtattg acatagtgtg gtttgtttac atgattatgt ccttgtttgg gattgtaaga       360
ctcaataaat ttttcccctct acgaaacagg gatcttagcc aagctgagag gcgcaagtat       420

```
gggattgagg ataacttggt tcgtttcagc ttcggagtgg aagactttga agatttgaag    480
gctgatgttc tgcaggcact ggagaccata taatggcgct aatctccgtc gtttgggttt    540
gggtttaaat gaccggccta gttattttgg tgtttcaatt ggtatttgag ctctctgaag    600
ttcgtgtttc attttaggtg gatcattgac cccccggtaa taaattggaa ctttgtttgt    660
aatcccatca atggggggat tgattttcaa ttttttttatg agtgtttatc aggggattaa    720
gcaaacaaaa ttagaaagaa gcctgnnnnn nattngnnnn ngggggnntt nnnnnccctn    780
nnnnnggnnn ntggnntgta aa                                            802
```

<210> SEQ ID NO 65
<211> LENGTH: 624
<212> TYPE: DNA
<213> ORGANISM: Gossypium hirsutum
<220> FEATURE:
<221> NAME/KEY: n = a, t, c, or g
<222> LOCATION: (1)..(624)
<223> OTHER INFORMATION: n = a, t, c, or g
<400> SEQUENCE: 65

```
cttctcaccg ctcttccgga aatcgtcact ctctntcacc aggtatgttt cttnctcttt     60
ctttaaagct tcttctgcaa tcttatgggc aaaagcattt tctgttctgt ttataaactg    120
gaagctaata tattcaaaac tagtcatctt actatggatg tctttaataa tcgcccctat    180
gactgattta tcgttcttca tggcttgaca tttcttgatg attgtgcgag aatcccccat    240
gatcgttact gagggaaaat ccattgcaat tcctagtttt aacgcctgta gacctgcaaa    300
agcttctgca gcaaatggaa acgggacatt cctgtgtagc tgagtcttca tagccntaag    360
tctccctgac cagccccaaa ccgccagtct cgatgcctat ttagagttcc ttttatcaaa    420
agttgcatcg aactgaatcg tcactttggt ataaacctcc tgatgcctgt aactgctact    480
cgtatttaag gtacttnctc tttcccgcaa cccttcaagt ttggctatgt acttttgaac    540
nttgagtgtt aactccctcc ctgtctctgc tttctgttca tgtataaatt tattccttaa    600
gctccaaata aaccacatac cgca                                          624
```

<210> SEQ ID NO 66
<211> LENGTH: 774
<212> TYPE: DNA
<213> ORGANISM: Gossypium hirsutum
<220> FEATURE:
<221> NAME/KEY: n = a, t, c, or g
<222> LOCATION: (1)..(774)
<223> OTHER INFORMATION: n = a, t, c, or g
<400> SEQUENCE: 66

```
ctccctcgac accactattc tactagaaac ggtgaccgac gaagcgtaga ggtccgattt     60
acaaccaaga ctcgaaggct gccaatttca gccttgaaat cccctccaga actccgattt    120
gaaggagaag attccagcng cctatttgcg aatgtaaacc taatttgaag attttatgta    180
aagagatttt taattatctg atctctgtct ctgctgctat attttatttt tggttttcta    240
tcctactgct cgttattccg tctgtttact tcgttgagaa ggagaatttt ttttaaagct    300
atcagtttag tgtcaatagc ggatttgcgg tcgacactgt gaattagcgg ctgcatcacc    360
gctatttgaa actctgactt gctattaatt ttggatatt attgcagctt caaatggaag    420
gattaagcgt agcagatgct aatttgttga tgtatttaca cccatcaaag agtaggaacg    480
tgtctcagtc gattctccgt gagcttggct ctttgctatt caagttagtt cttttacttt    540
```

```
cacttaaatt taattttcca taaactcaa aactcctgtt tttgtttatt attttttctt    600
caccaaaagc tgttttgtgt tgatattgct tttgatttaa ataaagtata ccttaattta    660
gtttggtctg ttttctagtt tagctgaaaa tttaacttct gatgatgaag ctaatgatac    720
tgtggctcnn nttaaacaaa tggagaagtt tattactgtt gagaatataa gctt          774
```

<210> SEQ ID NO 67
<211> LENGTH: 170
<212> TYPE: DNA
<213> ORGANISM: Gossypium hirsutum
<220> FEATURE:
<221> NAME/KEY: n = a, t, c, or g
<222> LOCATION: (1)..(170)
<223> OTHER INFORMATION: n = a, t, c, or g

<400> SEQUENCE: 67

```
ttagacattg gcgatctgct tcatttcttg cttcgtcgct tggttatcn gatgcgagtt     60 tcatctctct cagtctctct nagtgtcttt cttttgtct tcatctttc tttggaaaaa    120 agttgcgtaa ttttgttgtg aatgttcaat tgttgtttcg cttttttttt              170
```

<210> SEQ ID NO 68
<211> LENGTH: 551
<212> TYPE: DNA
<213> ORGANISM: Gossypium hirsutum
<220> FEATURE:
<221> NAME/KEY: n = a, t, c, or g
<222> LOCATION: (1)..(551)
<223> OTHER INFORMATION: n = a, t, c, or g

<400> SEQUENCE: 68

```
tttgggcctg gtttatccta tctaggtatt gggccctgtt gtaaatgggt attcgggttt     60
gggcctattg taattgggtg tggtatttgg gttttgatng gctgtaaatg aactttatat   120
tttggactat cgtttattgg gcnccgggct aaaattgggc cctacaacta taatgcatat   180
tttattatat taaaaaccac aaataaatat aataaatatt tttattgtat taaatataat   240
ttttaaaatt ttatactttg ggttcgatta tttattggat cnatttttt aagttttgga    300 taatcgattt aattgttatt ggattaatna tttaatatat ataattattt aacatatata   360
attaatataa tatttttat aacataatat attcgggcta ggtttgggtc aaaaaatct     420 tacccaatgc tcggctcata taaaaatgg tcccaaattt tacaaaaaaa ttatttttta   480
gattttgtat tttattcaaa cccttttatt ttttaggtaa attttnaaat ttataccgat   540
gacccgatcc a                                                         551
```

<210> SEQ ID NO 69
<211> LENGTH: 635
<212> TYPE: DNA
<213> ORGANISM: Gossypium hirsutum
<220> FEATURE:
<221> NAME/KEY: n = a, t, c, or g
<222> LOCATION: (1)..(635)
<223> OTHER INFORMATION: n = a, t, c, or g

<400> SEQUENCE: 69

```
agttgctggc tggggactgg tcttangctc ggaagtgaat cctcangcat cacatattcc     60
actcacagaa atattggaat tgcccttttc gttcttgcta ctgtgcaggt atttcttcaa   120
ttactaaatc tttcatgccc ttttaacatt tgggtcatt cttagaattg tgcgaatcaa    180
gtttaattat ggtggtgtga cactgaaact tgggaactta ttgtgtcttt acttgttaga   240
tttttgcctt gtttataagg cccaagaaag atcacaagta tagattctac tggaacgttt   300
```

```
accaccacag ctttggatac gccatccttg tccttggcat cttcaatgta ttcaagggta        360
tcaatatctt gaaacctgaa gacaaatgga aaacagctta tatgattgtg attattgcct        420
tgggtggtat ttcattgctg ttngaagcca ttacttgggt tgtcgttttg aagagaaaat        480
ctagaaagtc caccaaacct tgcgacggat acaacaatgg ccaaagttga tggcatcagc        540
aagcctccaa ttgcagattt tgtaacaccc ttgtgctttc tcatccttgt tgggatgttc        600
tatttcctat tttcagtgtc ttgtataatt gcttg                                   635
```

<210> SEQ ID NO 70
<211> LENGTH: 583
<212> TYPE: DNA
<213> ORGANISM: Gossypium hirsutum
<220> FEATURE:
<221> NAME/KEY: n = a, t, c, or g
<222> LOCATION: (1)..(583)
<223> OTHER INFORMATION: n = a, t, c, or g

<400> SEQUENCE: 70

```
tggagggaca gagatcatct ggcacagcag gagaaacccg tcttggaagc atttgcccca         60
tccttgacta gggtgacttt attcccagac aactcacctt tatatgaatc agagtttagg        120
gcttttcggc ttacattgtt gtagatttcc cggataacga tctcnaaagc agtctgaacg        180
ttagtagatt cganggcaga cgtttccagg aagaacangc cttcttcctc tgcgaggctt        240
ttgccttcct ccacacttac atctcttatg ttctccaaat cacatttgtt ccccaccagc        300
attcttgtca atgtagtntc acaatgagct gcaaggatta attacaataa ggttcaattt        360
ttttnacttg aatnaaacaa angaatgtca tttaatttag tttcctagaa agtgaaaact        420
tttctaggaa taaattttttt tctcatagct taaacaattc ctcttntccc tagaccaaga       480
agaaccatgg gcaagtacta acttttttgca cagaatctaa aaaagagct ttttggtata        540 aagatcataa atctaagaat agacaaagaa aatgtaaatc taa                          583
```

<210> SEQ ID NO 71
<211> LENGTH: 572
<212> TYPE: DNA
<213> ORGANISM: Gossypium hirsutum
<220> FEATURE:
<221> NAME/KEY: n = a, t, c, or g
<222> LOCATION: (1)..(572)
<223> OTHER INFORMATION: n = a, t, c, or g

<400> SEQUENCE: 71

```
taagggcat acccttatta gatatttgct tgatctcata acccaacacc ccccaaaaag          60
aaccctaatt tgttatcaac tttcatatct caataaatca tatagtatat cccccctccc        120
catgaataac cctcaccatc tgaaccctac ttctctaaaa tccaggttca ccacgaggtt        180
cctccgcgcc ctgactaaaa tccgtgctca aaaacctatc tcctcgtctt ctcccacaga        240
gatcttccga cggtatcgaa ggatcaaggt tgcagctgac aagtccatgg cttactccgt        300
taggtcgagg agaatttgga gtaaggcaat gctttggaag cttcgaagcc gatcttatng        360
tcgtcaagac ccttgttcag gcagaagatc tgggaagact aatcaagcca tcatgaaaaa        420
atcaagtaac gagaatacta caacaagaag ggaagatggg gttgggtttg ttgaagaggc        480
agatgaacta agacagcttg ttccaggtgg tgaaaccatg aatttatgca acttgttgga        540
tgagactgca cattacataa agtgtcttac ca                                      572
```

<210> SEQ ID NO 72

```
<211> LENGTH: 464
<212> TYPE: DNA
<213> ORGANISM: Gossypium hirsutum
<220> FEATURE:
<221> NAME/KEY: n = a, t, c, or g
<222> LOCATION: (1)..(464)
<223> OTHER INFORMATION: n = a, t, c, or g

<400> SEQUENCE: 72
ataagccctt tagactccat cccattgcac catttaactt tcctcacgtg tctgtaaccg        60
atacaatgga ccctcagtcg ggtanggctt ggtcagaacc ctaaagtttg ggaggagccg       120
ggcaagttca agccagaacg tcacctccag catcgtaata aaggcaaaga agcggtgctt       180
gctgagccag atttgttgtt attaacattc agtagaggaa agagtgggtg ccccggtgtg       240
gtgcttggaa actcaatgac taccatgttt gcgaggcttt tgcaaggttt tgattggagc       300
atcccggcta atctggcaag cattgatctt agtcaagaaa agggagagta atttctggct       360
aaaccattgc ttgctattgc aaggccgcgg ttgccaccct ctgtctactc gttttctggg       420
taaataaaag agagagaaag agaaagacag tgatgtttac agga                       464

<210> SEQ ID NO 73
<211> LENGTH: 661
<212> TYPE: DNA
<213> ORGANISM: Gossypium hirsutum
<220> FEATURE:
<221> NAME/KEY: n = a, t, c, or g
<222> LOCATION: (1)..(661)
<223> OTHER INFORMATION: n = a, t, c, or g

<400> SEQUENCE: 73
ctcaaccatc aggagtaagt ttggtcctaa aaacacactt cactccaatc acctttctgt        60
ttgcaggtca cccaactagc tcccatatct ggttttctt tatcatacct agctcttcct       120
tcattgcctc catccattct tgatcatctt tggcttcntc atacccaaca agttcaagaa       180
caaccacact acacctttga taaacttcat tcaatnatct tgtacctcta gttgatgtat       240
catccaccaa tttattagna ctgagagata actcttgctt ctttacttca gtgtcacttg       300
tccgatccca ctgttcatct tctgggaact agaaatctct acttccaatn attttccttg       360
cctgaggtta atggattctg tagncttta acaccaagtt ataactaaca aatatttcat       420
gctcagatgt ctctcctaac ttgtccctct taacctgtgt aacatgacag aatcataaac       480
aaccaaacat attcaaaatt ttcagagttg gtttcatctc aaaaatattt catgcttaga       540
tttctctcct aacttgtccc tcttaacctg tgtaacatga caaaatcata aacaaccaaa       600
catattcaag cttcataagg tgttttcttc tctaanatcc tcatagacag gctattcagc       660
a                                                                     661

<210> SEQ ID NO 74
<211> LENGTH: 472
<212> TYPE: DNA
<213> ORGANISM: Gossypium hirsutum
<220> FEATURE:
<221> NAME/KEY: n = a, t, c, or g
<222> LOCATION: (1)..(472)
<223> OTHER INFORMATION: n = a, t, c, or g s

<400> SEQUENCE: 74
nctngttcat ccgttgactt aatgaatgtt tttatcttag ctttccaata ctcataattt        60
gttccacgat catagatcgg catgagacta aagatccttt cattacaagc aagcatatca       120
accaagataa tcactatta tnttgagtaa gaggctctga taccaattat agaaaagagt       180
```

```
gagtacttgt tttacaaaca taaactgtgg ctaaaatagt gcttngaatt atggtcacag    240
tttcaaccac aaaattaaaa gtgcaaaaat gtaaanatga acattgagat tgtttacata    300
gttcgacttc aatctacatc ttcanggcct tgcctagagc gatgatacac tatctttatc    360
gcaatcaacc aattatttaa gtcttaacat caatataact cttacnaatt taacgacctc    420
accattgtac aaagactaaa tcactctctc attaagcttc tgcctcaaaa aa            472
```

<210> SEQ ID NO 75
<211> LENGTH: 662
<212> TYPE: DNA
<213> ORGANISM: Gossypium hirsutum
<220> FEATURE:
<221> NAME/KEY: n = a, t, c, or g
<222> LOCATION: (1)..(662)
<223> OTHER INFORMATION: n = a, t, c, or g

<400> SEQUENCE: 75

```
gatcgttata gcttaaccta gctagcgcgg ggactaantt gcaaaatgat tttaggtttt     60
tgaagtttaa tggaagaaaa tgaatctttg ttgttagtta aacaacttttt gttaagtgaa    120 tttaatgaa attgtcaatt aggggttaat ttgaaaaatg tgaaaattgt gtgttaaatg     180
tgtgaaattg tgaaatgcat gggcttctat gagcatatag gatatttggc taggcttaga    240
tgnggtgaaa ttgcatgaat ttcattttnn cgagcctaaa gactaaattg taaagaagtt    300
aaaagtgtag gggtaaaata gtaattttgc caaaacatga attttggatt gaatagaata    360
gaataaagat taaagtagtt aaatttgatt atatagatca agaaaagcaa cgtacagaat    420
tagatcgagg aaaagataaa gtattggatt gaacgatcgt tttctgtcgt acgtgttcga    480
ggtaagttcg tgtaattaaa ttgcgnattt gtatgattta attgaatata tgtatatgaa    540
tggtttaatt attttgtata attatcaagc atataaccga cgacgtacga agaatactga    600
gccccgtttg aaccttagga attcgtagga tacaaataac atgtcattag ggttaccgat    660
tc                                                                   662
```

<210> SEQ ID NO 76
<211> LENGTH: 711
<212> TYPE: DNA
<213> ORGANISM: Gossypium hirsutum
<220> FEATURE:
<221> NAME/KEY: n = a, t, c, or g
<222> LOCATION: (1)..(711)
<223> OTHER INFORMATION: n = a, t, c, or g

<400> SEQUENCE: 76

```
cttttttgcct gttgggtctt agtttaganc ancaagggtc gaaactgaat ttgggtttgt    60
tgctccccca ttccccaccg ttgatgagtt gattgttttg ccgtttggga gctttccacc    120
aagtgtcggt aatatcaatg gggttagttg atgacaacaa gaacaaggag aaggaggcaa    180
gcgaggatga aggaggagct gcaagggggtg gtggcagaca aatgagtgat gattcctctt    240
tctataccac tgatcaggag gaggataacg atgatgagag tgcacttcaa ttgggtcccc    300
agtgtagtct caaggaacag cttgaaaaag ataaggttta aacttttcat ccnctttctt    360
tcacttggat ttactcaaac tctcatgcat gtatagttgg aatttgtctt tttatcatca    420
tttgcttgag ttgtaggang atgagagctt aaggaaatgg aaagaacagc ttctcggaag    480
tgtggatatt aacaacattg gaggtaccgc tttcatttct ttttttcttt tttttttaaat   540 cccttttgaaa cataggtttc tgtataattc aattgtatgg catgtttcag tactattgct    600
```

```
ctggctctgg gaaaattaaa acaaacaaat ctttcatgca agtcttaann natctgcnnn        660
atttgacatg aatcaaaatn nntngaattt tggatgnngt tntnnnnntt g                 711

<210> SEQ ID NO 77
<211> LENGTH: 592
<212> TYPE: DNA
<213> ORGANISM: Gossypium hirsutum
<220> FEATURE:
<221> NAME/KEY: n = a, t, c, or g
<222> LOCATION: (1)..(592)
<223> OTHER INFORMATION: n = a, t, c, or g

<400> SEQUENCE: 77
tttttgaaga atctatgtgt ggagcangcg ccacagactg accatcactg ccatctttct         60
tgtaaagatg gttcagcagc gtatgagaag gctttcgcaa ggaccgggga ttcctaacaa        120
aaagtgattg ctcatctaat atctttgtcc gaagctgtgg aggcagttca ggnggaggct        180
tgctgaaatc accatcattt agtggttgac tgtcatagct tgatatcgga gaaggtggag        240
attcgaactc tgaaaggctt tcaggagctt ctggaacaaa ctcctgttac aacacaccaa        300
gagagtctca tttttaatgt tggtattcaa gcaacaaatt aagtaaaatg catcaaagaa        360
tcattacacc atagctactt aaatatatga agaatactct caacttccta gtcttgaaag        420
ctgagaagat agcaatagag atgccatgaa cacttccaaa tcataattat gcgttataaa        480
gtcttagcaa ctagcacgca tcatatacgg gctgatgtca ttgatatgta agtagcanat        540
ttatatcaca ccattgaaaa cacaagcatg atagcagata tggagtcctt gc                592

<210> SEQ ID NO 78
<211> LENGTH: 610
<212> TYPE: DNA
<213> ORGANISM: Gossypium hirsutum
<220> FEATURE:
<221> NAME/KEY: n = a, t, c, or g
<222> LOCATION: (1)..(610)
<223> OTHER INFORMATION: n = a, t, c, or g

<400> SEQUENCE: 78
atttataaac gacttccttg ttgtttgtaa atcatcctaa actgttgtta cttaataagt         60
ctngaatnng tttggaaaac atattgatat aattanttag tttaaaattg ttgttcgttt        120
acgtctttca aattcnatca aatgtcttac agcggngttt ctttggaaac ngttattttt        180 ggaaaaccg ttgccttcaa aattaccgtt ttatcagtca ctatgctaga aaccaaaatt         240
aaagtttaaa cctaaaaaca atccaaaaag tttggagagt cccaaaatta caaaactctc        300
aaaaatcata aagttaggta aatttatga aaatgaagtt tacagaanag tggtcacaac         360
tgagctttcg tcgcaccaac ctgcctaagt ctgaaggtta cctaaacata atagacaaat        420
agagaatgag ttttttgacaa ctcagtgtgt aacgcattta tgtaaacaga attcaaattc        480
aatcttttgc agaatcaaaa ttatacagat acagacatgt ctaatcctac cctcatcctc        540
tacacaccaa ctctaaccat cctaacacac cacgtggggt ataaaacacc catccagccc       600
tacacaccgc                                                              610

<210> SEQ ID NO 79
<211> LENGTH: 608
<212> TYPE: DNA
<213> ORGANISM: Gossypium hirsutum
<220> FEATURE:
<221> NAME/KEY: n = a, t, c, or g
<222> LOCATION: (1)..(608)
<223> OTHER INFORMATION: n = a, t, c, or g
```

<400> SEQUENCE: 79

```
caaaatatgt agaatttcac gcagttcaat agcaatataa tacttcaatt aatcaatctc    60
aaaaacacac aagaaattgt cgaattccac aaaatccaac agcaatgcga taacaaaatt   120
aaacagtttc ataacacaca ccttaaatan aaaccttgat gccaagactg atcgattcgc   180
tcccactaaa ccattcnaaa acccgattta gaaagcaatt agacngaaca cacgaagatg   240
actaaccctt aaccaatcga taagtaacat atatgtaaaa actaaaaaga ataagaaaag   300
aattgaagaa cagaaggaac cccaacaaaa ttctaaaaat ttgggaaaca aaggaaaca    360
gtaagagaag aacgtnaaga gaaagtaatg gaaaaaaacg tgatatttgt tttatgagaa   420
caacttcttt ttgtaaaaaa taaaataaca aatacttaaa tagtttaaca caaaatcaaa   480
acataactta aaccaaaatt cgaataaaac caattattct ttaacacaca tgaggattca   540
aacctgagac cngaaggtaa actaacacac atccaaccac cgaaccaaca atctcattcc   600
gacattag                                                            608
```

<210> SEQ ID NO 80
<211> LENGTH: 655
<212> TYPE: DNA
<213> ORGANISM: Gossypium hirsutum
<220> FEATURE:
<221> NAME/KEY: n = a, t, c, or g
<222> LOCATION: (1)..(655)
<223> OTHER INFORMATION: n = a, t, c, or g

<400> SEQUENCE: 80

```
tggagactga cattccggtg tnaaaccgtt ttcattgcca tgagtcgtcc gccctgccc     60
cagaccacca ggctggatgc cgacttaaaa ttcctactat caaatgctgc gtcgaactga   120
atcgtcacgc tggttcttcc ctcttgatac ctgtgactac tactcggttt taaggtattt   180
cctttcatcc tcaaccctc gagttcagct atgtagtttc aaactttaag agataactcc    240
ctccctgttt ctgttttctg ttcatgtatg aatttattcc ttgagttcca aataaaccac   300
atgccacaac agtaaatctt acattgctca gaggtactcg ttctgaaaac ccaggtaatt   360
cattcccaaa atccttgaat cgtactttca ctgatccacg acagatctaa taatggccac   420
atttcaccta ttgcaggaca ataccctaaag atgtgggtga tgtcttcttc ccctcttcca   480
catcgaggnc atgccgcgtc attactcacc cgtttatgtt ttaaattagc tagagtaggg   540
atatagttct aagatattct ccatattgta attgctatgt tggcaggcag ttgtaaattc   600
catagcttgc cgtagaaatc ctttagatta gcctatatta aataaaaatt aggat         655
```

<210> SEQ ID NO 81
<211> LENGTH: 549
<212> TYPE: DNA
<213> ORGANISM: Gossypium hirsutum
<220> FEATURE:
<221> NAME/KEY: n = a, t, c, or g
<222> LOCATION: (1)..(549)
<223> OTHER INFORMATION: n = a, t, c, or g

<400> SEQUENCE: 81

```
ctcgtcacct tcttccctgt taagtatttt cttttttggat aaattacatc tgtagtcact    60
aaactattga taaatttatt ttttgatcac tcaactatga atagttacaa atagtcatcc   120
aactatttga tttttctttt ttagttact agttgttaaa tggctaacga aaagatgatn    180
tggcagcttt cagaattgtc ataataataa ttttaacct caacatttat anattgtttc    240
```

```
aatttagtct tgatcataaa aatttaacac tcattggtct ttttctttca aaataaaata    300
attgtccatg atctcggaac ttcattttca tccttttttg tctttgaaga cgaataagag    360
catgtttctt tccaagtcan ggacttcaat aggtcatgcc ttcctcgnat gaaccattgg    420
actcgtccgg acctatccaa catggctttc ttacgaatga tgttgcacaa atacgtttgt    480
aaatccaatg tgacaagttc gtattctaaa tcacccacca cgatatcttt catggattct    540
tcattgtcg                                                            549
```

<210> SEQ ID NO 82
<211> LENGTH: 634
<212> TYPE: DNA
<213> ORGANISM: Gossypium hirsutum
<220> FEATURE:
<221> NAME/KEY: n = a, t, c, or g
<222> LOCATION: (1)..(634)
<223> OTHER INFORMATION: n = a, t, c, or g

<400> SEQUENCE: 82

```
cacaaacata ggatataatg ccgatgccat atcccanaca tggtcttaca ctggctcatc     60
catcaagtcg atgccatgtc gcagacatgg tctgacactg aaacctcnat atgtgccgat    120
gcatgtccca gacatgtctc acagtagctc tcgtctcaat gcngatncca tgtcccanac    180
atggtcttac actngctctc ataatatggt cgatgcatgt tctagacatt tcgtacactn    240
gcacacaaat aacccgaatg tcatggcatg aatatttgat ttatttccta aggttcaaac    300
aggagttcta ctgtaacatc ccgaatgagg gcctagtcag aatagtggtt ttgagaccac    360
aaatatgatg ttaaaataat tgtttcatga tcattatgag gtctaggata tgaaaatgag    420
catgtgttaa agtttcataa agaaattcta tgtgtaaggt gtcctattgg aaattaggga    480
ctaaattgaa taaattgcaa aacttggatt ctagaagtaa tttgtatgaa attgctttgg    540
aatgttaatt aggagtcctt aaagagtaat tttcccaatt tttaagtttt tggacaaaaa    600
tgggcatgca tgaaaaattt tggaagttta gtag                                634
```

<210> SEQ ID NO 83
<211> LENGTH: 681
<212> TYPE: DNA
<213> ORGANISM: Gossypium hirsutum
<220> FEATURE:
<221> NAME/KEY: n = a, t, c, or g
<222> LOCATION: (1)..(681)
<223> OTHER INFORMATION: n = a, t, c, or g

<400> SEQUENCE: 83

```
tgtttctgaa accactcnga atgtcaatcc agcaggtgag atttcctttc ttttttcttg     60
gttntgggga tgtcctgtac tatgtgaata tatggaattt aactgaagtg atataatggt    120
gtatgtgtaa aactcgcact acttgtgcat tatgcaaaac gtgagtgtgg acatgcacga    180
agctaatttg acaagcatgt gttctgtttc tcaagtattg tatcaaaata ggaaacagta    240
gactggaact ttgagaactt ttgtaagtgt ttctctttta cgaatgttgt catgattttt    300
gtgattagga tcaagggctc tagagcttgg tatgatgaac aaactaacaa gatcctcaaa    360
actgctggat ggatcatctg attttgtgct cacttacgag gacaaggagg gggactggat    420
gcttgttggg gatgttcctt ggaagtacgt atagtttcag ttatacgtgt tgctttacat    480
tttcattttc ctatggtttt gctcacatga gatttataaa accaactact gttttgcttt    540
atctccagtt aggaaaccaa atgtaggatc tccattagtt tcactttgcc tacatgtgtt    600
gaatgaattt taaactatgg aagtgcatat tctctcttta g ccgtatatat agttgcattt    660
```

| | |
|---|---|
| atnngannnn ctctgcggtt c | 681 |

<210> SEQ ID NO 84
<211> LENGTH: 667
<212> TYPE: DNA
<213> ORGANISM: Gossypium hirsutum
<220> FEATURE:
<221> NAME/KEY: n = a, t, c, or g
<222> LOCATION: (1)..(667)
<223> OTHER INFORMATION: n = a, t, c, or g

<400> SEQUENCE: 84

| | |
|---|---|
| aactcagata ccgtccatta tttccttcac tgaagtggtg aagctgactt ttcttactat | 60 |
| ttattttaaa acttaaaaca tattctaatt ttattaagta taaacttact acaatttaat | 120 |
| tacgttaaaa ctttgttaaa tcatcaaaac tcttaagctt caacatcctt caaacattaa | 180 |
| agtccttcag aaccaaatat agatattgcc aatcaaaagt gaacatgtat ttttttcctc | 240 |
| tattctttat ctattctact atttgttttc tttttaattc attttctcca tgtgtaattt | 300 |
| ttaactgatt tttgtaacag attagccagg gaagtagnga gctaatgtct aatgatgact | 360 |
| tctcatttca aactttgttt tattttgaaa tagattagta agtgaattgt tagacttgaa | 420 |
| caacaatttg agtttataaa acaaattata ttaaaattta tctaaagtaa ctatttatta | 480 |
| tatattacat aaaatttcat ttatatttta catatatatt tttatatgca tgcgccttat | 540 |
| tttactctgg cgagtgcttt tattttgtgt cttgtgcctt gggccataca gcagacttag | 600 |
| agagtgcacc tagtgccttt gacaatggta gtttgaagat atagtcgtcg aatgctgttg | 660 |
| aaatatc | 667 |

<210> SEQ ID NO 85
<211> LENGTH: 648
<212> TYPE: DNA
<213> ORGANISM: Gossypium hirsutum
<220> FEATURE:
<221> NAME/KEY: n = a, t, c, or g
<222> LOCATION: (1)..(648)
<223> OTHER INFORMATION: n = a, t, c, or g

<400> SEQUENCE: 85

| | |
|---|---|
| gtcatctgca aagaacagat gcgaaagatt cggacctata cgngataaat gaataggact | 60 |
| ccactcccct gcatagatgc ttcctgaaat ctatgtctca accattccat acagaaaaca | 120 |
| aagaggtatg gtgacagtag nnatccttgt ngaatatccc ttactgacct aaactttag | 180 |
| gttggcacac cgttctatag tacctgcata gaagataaan atatagcatc nataataact | 240 |
| ttaaccaaaa aaggangaat acctataaca tttagggagg cctcaataaa atcccatcta | 300 |
| actctatcgt aagccttttc caaatcaata ttgactgcca tcnattggag tctcttctta | 360 |
| gtcctcatac agtgtaaaac ttcctaagcg ataatgacgt tgtcaataat acttcttcta | 420 |
| gctataaagc ctgctngctc ttggcctatg atcttcagaa aaatactctt aaatctatta | 480 |
| gcaatgacct tcatgaccaa tttatacaac accgagcaaa gactaatagg cctaaattaa | 540 |
| gaaaattttt tcgagttttg gantttgggt attaacacaa taagtgtatt attgaactct | 600 |
| ggatcgatga ttcctccttc gaacactttc ttgacccact cacagatg | 648 |

<210> SEQ ID NO 86
<211> LENGTH: 617
<212> TYPE: DNA
<213> ORGANISM: Gossypium hirsutum
<220> FEATURE:

```
<221> NAME/KEY: n = a, t, c, or g
<222> LOCATION: (1)..(617)
<223> OTHER INFORMATION: n = a, t, c, or g

<400> SEQUENCE: 86
cctaaatgat accattgacc attccaacat ataatgaaac aaccatcgga aaattacaag      60
gaaaaagag aaactccagt ttacaaatta cccttaccca tttattggtg tggagaggac     120
cgatgtttat tgctccattt tggtagacca caaggtcgan ccttgaatga aggccatcaa    180
tgagggacc taaaatgaaa ccacaaccaa aaagcgagag agagatggaa ggccatgagc     240
tttttagact tctcttgcgc tgttttctta cagtgcaaca atttatagaa ggggaatgtt    300
tgaaattaac atttagagga agtttaggaa gcagatgaga ggaacttaca gcgatgaggt    360
tgggcatggt ttaccatccc ctcaagtttt gcgactgcta tatttcttca ttttcagatt    420
gagctanngt taaatctcaa ccacataagc aattgtgttt ttgggtaaac tactagttgg    480
tcacccaact tttagggtga ttttatttttg gtcacccaaa atgaaatcct tgcaatttca    540
tcattcaact tttntgacac gttcatttta gtcacacaac cgtttaatttt ctaatggcag    600
ttatcttgta catgtca                                                  617

<210> SEQ ID NO 87
<211> LENGTH: 607
<212> TYPE: DNA
<213> ORGANISM: Gossypium hirsutum
<220> FEATURE:
<221> NAME/KEY: n = a, t, c, or g
<222> LOCATION: (1)..(607)
<223> OTHER INFORMATION: n = a, t, c, or g

<400> SEQUENCE: 87
tctggtttgg tgnataatga ggtatttctg cttcatctgg ctttgcctga gggccgtcag      60
ccggtattcc atcgaaacca tatttagatg aagcatcgct ataatcgcca gccgaagcaa    120
taactagcaa tgaaagtaga agtaaggaga atggcaagga gagacgtggg agagccattg    180
cgatgtagtt actatatgaa caaagaaagg aagatggtgg ctgaagaaat cggctcacaa    240
cgttgcctat ttatagggaa atttgttacc aatgattatt gattatgatt agtagttagg    300
aaataaaata aacaatgtag gaacattacg ttgggtgcac gatcccaacg tgatttgtag    360
actggggtac cactacctaa ataatctata tctaatgtac atggacacct tttcctgcaa    420
ccctaatgaa gatcgtcaaa tgctatgaaa atatatacta aaatcttgtt aaaaattaac    480
cgtaaaaaaa ttatatgcct gaagttacat atctattaca ggcaaaaaag cgcatcaccn    540
agaaggaaaa aaggaaatgt aataggcagc ttgaaacctg ccaggttaag gcaaggacac    600
gtcatag                                                             607

<210> SEQ ID NO 88
<211> LENGTH: 775
<212> TYPE: DNA
<213> ORGANISM: Gossypium hirsutum
<220> FEATURE:
<221> NAME/KEY: n = a, t, c, or g
<222> LOCATION: (1)..(775)
<223> OTHER INFORMATION: n = a, t, c, or g

<400> SEQUENCE: 88 tttcatttt aatgtttaag tttgtattat aattaaaaat aataatttaa ttttttttaa       60
aggttgatag tccaattcta cgccttttaa aggttgaga actaaattta actaaaaaat     120
aagtgcaagg ttgtttgaac cggatcgnat aaactaattg gattagttgg atcgagaacc    180
```

```
cattgggta ctaattcgga gaaaggcatt gatctgtttt actcgagaac cagtatagat    240
aagttgaata ggcaaaaatc gattgaacta ggcttttaat atatacattt tttnnnnnnn    300
natgaatttt taaagattta tttaattgaa ccaaacggat cggttagatt gaaaaactgg    360
tggtttaact gattcgacct ccggttcaat tttaaaaacc ttaaataagg cttaatttg    420 ataaaagatg taaatataaa gtgttaaatt tatcattact ctgtgtgaat aacttctaat    480
atnctnngta aattttaatt aattaaaata tttataatat taactcaaat ttttttnnna    540
aaatgacaaa aaaaattac tatagaagtt aagggcaggt aatgaccttg gtaaaatgag    600
ataactgtaa atttaggctt tttagaataa ttaattactt aatttaagtt ttttaacccc    660
actaattatt gaaaaaatta tatagtcgac ccctccaaaa aataacattt taatttaaac    720
cttttatttt tttaactaat ttaaaccgaa cttttacaaa atcgtattac actaa         775
```

<210> SEQ ID NO 89
<211> LENGTH: 585
<212> TYPE: DNA
<213> ORGANISM: Gossypium hirsutum
<220> FEATURE:
<221> NAME/KEY: n = a, t, c, or g
<222> LOCATION: (1)..(585)
<223> OTHER INFORMATION: n = a, t, c, or g

<400> SEQUENCE: 89

```
ataatgaggc tcttgtcacc tgaatccaaa gagaatgaga tgaatgttag ctatctagaa     60
tcccaaatga aatccaagga ggaacccaaa acagccaaga tagaaacata tcattatttg    120
gctaaaacca agtttgacga aagaagaan atagcaactg aggagcttgt cgtgatggat    180
gttcgaaaac aacattcagc agcaaagaga cagatttggt tttggttagc tttggtggta    240
ctgctgctag ctttgcttgc caattgctta ctccaatcta attatgtctc taacagtgtt    300
tcttttgttt tcccatgaa ataagaatag aatcatctgc accgatagac agctgccaga    360
aaatttaatt aattaaataa ataaaccaag tttgtagatt tcatttaact gaagtatttt    420
tgaacgttaa taaattcgcc accaaccta taaaaggcta caaatatggt tgaacggnga    480
gaaattaggc ttagtttgna tgagcnataa atttacctct ggtgaggtta aaaatagtgg    540
tggcggtgag attaattant gaancggtga gttagaaaca atgat                    585
```

<210> SEQ ID NO 90
<211> LENGTH: 604
<212> TYPE: DNA
<213> ORGANISM: Gossypium hirsutum
<220> FEATURE:
<221> NAME/KEY: n = a, t, c, or g
<222> LOCATION: (1)..(604)
<223> OTHER INFORMATION: n = a, t, c, or g

<400> SEQUENCE: 90

```
tatgcaagca cccgtttgcc aatgaacctt gacgagtttc acttgggaga ctgttttta      60 attaacatna catacggaga gggcgccatg ttcttcagaa gaatcagtcc caagtactaa    120
caccattttg caactcagcc aatagagatt tcatcaactc ttgtggccac catattcgga    180
cagacaggag ggatcgtctt acggcagaca tgacacctaa atccaataat cttgcttttg    240
ttccctgaat taagcccata agcatctcca tgaaaccatt ctgcataaat taatttaaag    300
gaatattatg aaaaagtata aaggaggaaa ttttttcaag catcagtagt cgatgtctat    360
aataataggc agtcgcctac agtgaactga tataaaaatg ctgaaaacta attacctcca    420
```

```
caaatttcac atgcaatata gcttgaatta gatgcatatc ctgattcaca acaaagaaaa      480
catctgngtg gatcagggga gacaatctta tgctcggaag gatcaaaaac cattttctt       540 tgaaattgca tcacccgctc atcatttggc ttactagaca accgaagacc attaagccag      600
aaac                                                                  604
```

<210> SEQ ID NO 91
<211> LENGTH: 644
<212> TYPE: DNA
<213> ORGANISM: Gossypium hirsutum
<220> FEATURE:
<221> NAME/KEY: n = a, t, c, or g
<222> LOCATION: (1)..(644)
<223> OTHER INFORMATION: n = a, t, c, or g

<400> SEQUENCE: 91

```
caatggaacc cattattatc aatcaaattg gattatgcta gcagtttgca cgataagttc       60
cgcatgggac atggatggta tgatgacggg cgggaagccg ataagggtca cccattgctt      120
caacataggc tttaatatga ttcttacgtt gtaatttata aatttaccng ccatgcattt      180
aatttatcca tgttgggcca atttattttg gaggcctaaa cttttttattt cactattttg     240 atcacgcagt gtttgttttt aatcctacat cttcaaattc tttctttttt gtaattgttc      300
attataatca gttccccttt tttttncata ttaattttttt ttnataaaat gagatttatt     360
ttgtnacttt taaatattat ttggtaaaat ttcaatgtct ttttcataaa tatttcttaa      420
aaagttttca agaatttttta attatttttaa ctatttttaaa tataaaatat ttatttatat   480
cataaaaaat taacatcaat tatatattaa ataaaaaaac aaattcggta tggtttcaag      540
taggcccgtc cgaaaaataa aaaagtttga ataaaaatat aggttcaaaa aatgggttta     600
gacaaaaaaa ataatgccca ttttctaaat gggctgaacc ttga                      644
```

<210> SEQ ID NO 92
<211> LENGTH: 25
<212> TYPE: DNA
<213> ORGANISM: Artificial Sequence
<220> FEATURE:
<223> OTHER INFORMATION: Description of artificial sequence: synthetic primer

<400> SEQUENCE: 92

```
tttccttgcc tgaggttaat ggatt                                            25
```

<210> SEQ ID NO 93
<211> LENGTH: 25
<212> TYPE: DNA
<213> ORGANISM: Artificial Sequence
<220> FEATURE:
<223> OTHER INFORMATION: Description of artificial sequence: synthetic primer

<400> SEQUENCE: 93

```
agttaggaga gacatctgag catga                                            25
```

<210> SEQ ID NO 94
<211> LENGTH: 28
<212> TYPE: DNA
<213> ORGANISM: Artificial Sequence
<220> FEATURE:
<223> OTHER INFORMATION: Description of artificial sequence: synthetic primer

<400> SEQUENCE: 94
cattacaagc aagcatatca accaagat                                                28

<210> SEQ ID NO 95
<211> LENGTH: 35
<212> TYPE: DNA
<213> ORGANISM: Artificial Sequence
<220> FEATURE:
<223> OTHER INFORMATION: Description of artificial sequence: synthetic
      primer

<400> SEQUENCE: 95
acaagtactc actcttttct ataattggta tcaga                                         35

<210> SEQ ID NO 96
<211> LENGTH: 25
<212> TYPE: DNA
<213> ORGANISM: Artificial Sequence
<220> FEATURE:
<223> OTHER INFORMATION: Description of artificial sequence: synthetic
      primer

<400> SEQUENCE: 96
cgtgttcgag gtaagttcgt gtaat                                                    25

<210> SEQ ID NO 97
<211> LENGTH: 33
<212> TYPE: DNA
<213> ORGANISM: Artificial Sequence
<220> FEATURE:
<223> OTHER INFORMATION: Description of artificial sequence: synthetic
      primer

<400> SEQUENCE: 97
gtcgtcggtt atatgcttga taattataca aaa                                           33

<210> SEQ ID NO 98
<211> LENGTH: 22
<212> TYPE: DNA
<213> ORGANISM: Artificial Sequence
<220> FEATURE:
<223> OTHER INFORMATION: Description of artificial sequence: synthetic
      probe

<400> SEQUENCE: 98
acttggtgtt aaaagcctac ag                                                       22

<210> SEQ ID NO 99
<211> LENGTH: 21
<212> TYPE: DNA
<213> ORGANISM: Artificial Sequence
<220> FEATURE:
<223> OTHER INFORMATION: Description of artificial sequence: synthetic
      probe

<400> SEQUENCE: 99
cttggtgtta aaagactaca g                                                        21

<210> SEQ ID NO 100
<211> LENGTH: 19
<212> TYPE: DNA
<213> ORGANISM: Artificial Sequence
<220> FEATURE:
<223> OTHER INFORMATION: Description of artificial sequence: synthetic
      probe

<400> SEQUENCE: 100
cctcttactc aatataaat                                                           19

```
<210> SEQ ID NO 101
<211> LENGTH: 18
<212> TYPE: DNA
<213> ORGANISM: Artificial Sequence
<220> FEATURE:
<223> OTHER INFORMATION: Description of artificial sequence: synthetic
      probe

<400> SEQUENCE: 101
ctcttactca acataaat                                                     18

<210> SEQ ID NO 102
<211> LENGTH: 19
<212> TYPE: DNA
<213> ORGANISM: Artificial Sequence
<220> FEATURE:
<223> OTHER INFORMATION: Description of artificial sequence: synthetic
      probe

<400> SEQUENCE: 102
atcatacaaa tgcgcaatt                                                    19

<210> SEQ ID NO 103
<211> LENGTH: 23
<212> TYPE: DNA
<213> ORGANISM: Artificial Sequence
<220> FEATURE:
<223> OTHER INFORMATION: Description of artificial sequence: synthetic
      probe

<400> SEQUENCE: 103
ttaaatcata caaatacgca att                                               23
```

METHODS AND COMPOSITIONS TO SELECT COTTON PLANTS RESISTANT TO COTTON ROOT KNOT NEMATODE

CROSS-REFERENCES TO RELATED APPLICATIONS

This application is a divisional of co-pending U.S. patent application Ser. No. 13/059,135, filed Mar. 17, 2011, which application is a National Stage of Intetnational Application No. PCT/US2009/055019, filed Aug. 26, 2009, claims the benefit under 35 U.S.C. §119(e) of U.S. Provisional Application No. 61/092,649 filed on Aug. 28, 2008, each of the entire disclosures of which are hereby incorporated by reference in their entireties herein.

INCORPORATION OF SEQUENCE LISTING

A sequence listing containing the file named "pa_53664.txt" which is 70.5 kilobytes (measured in MS-Windows®) and created on Aug. 25, 2009, comprises 103 nucleotide sequences, and is herein incorporated by reference in its entirety.

FIELD OF INVENTION

The present invention is in the field of plant breeding and disease resistance. More specifically, the invention includes a method for breeding cotton plants containing quantitative trait loci that are associated with resistance to cotton root knot nematode (RKN), a disease associated with *Meloidogyne incognita* (Kofoid and White) Chitwood. The invention further includes germplasm and the use of germplasm containing quantitative trait loci (QTL) conferring disease resistance for introgression into elite germplasm in a breeding program thus producing novel elite germplasm comprising one or more cotton RKN resistance QTL.

BACKGROUND OF THE INVENTION

Cotton root knot nematode (RKN) is a destructive nematode which forms galls on the roots of cotton plants. The causative agent is *Meloidogyne incognita* (Kofoid and White) Chitwood, a nematode which can infect a variety of plant species. Nutrient and water uptake are decreased in infected plants, and plants may become susceptible to other pathogens, especially Fusarium wilt (Minton, N. A. and Minton E. B., *Phylopalhology* 56:319-322 (1966)). Consequently, yield is decreased in plants infected with RKN. In the USA alone, an estimated 10.93% of cotton yield loss in 2004 was attributed to RKN (Blasingame and Patel, 2005). RKN is widespread throughout the US Cotton Belt. Methods to mitigate RKN damage include rotating cotton crops with non-susceptible crops and application of costly nematicides. However, the most effective way for cotton growers to reduce yield loss and crop damage due to RKN is to grow RKN resistant cotton cultivars. Therefore, a need exists for development of such RKN resistant cotton varieties and for methods to accelerate development of such varieties. Genetic markers can be used by plant breeders as an indirect means to select plants with favorable alleles. A major RKN resistance locus has been reported on Chromosome A11 (Kai, W. et al. *Theor. Appl. Genet.* 113:73-80 (2006)). Breeding for RKN resistant cotton varieties can be greatly facilitated by the use of marker-assisted selection for RKN resistance alleles. RKN resistance in cotton has been reported in different germplasm lines such as Auburn 623 RNR and Acala NemX. However, commercial cultivars with RKN resistance are limited. Identification of genetic markers associated with RKN resistance is of great value in a cotton breeding program. RAPD, AFLP, and RGA markers for identifying RKN resistant plants have been identified in a study using near-isogenic lines (NILs) (Niu, C. et al., *Crop Science* 47:9.51-960 (2007)). Genetic markers associated with RKN resistance in plants have also included SSR markers (Wang, C. et al. *Theor. Appl. Genet.* 112:770-777 (2006)).

Of the classes of markers, SNPs have characteristics which make them preferential to other genetic markers in detecting, selecting for, and introgressing RKN resistance in a cotton plant. SNPs are preferred because technologies are available for automated, high-throughput screening of SNP markers, which can decrease the time to select for and introgress RKN resistance in soybean plants. Further, SNP markers are ideal because the likelihood that a particular SNP allele is derived from independent origins in the extant population of a particular species is very low. As such, geneticly linked SNP markers are useful for tracking and assisting introgression of RKN resistance alleles, particularly in the case of RKN resistance haplotypes validated to exist in the resistant donor parent. A need exists for a SNP based marker set for identifying cotton plants resistant to RKN. The present invention provides a SNP based marker for identifying plants resistant to RKN.

BRIEF SUMMARY OF THE INVENTION

The present invention provides a method of introgressing an allele associated with Root Knot Nematode (RKN) resistance into a cotton plant comprising the steps of: (A) providing a population of cotton plants; B) genotyping at least one cotton plant in the population with respect to a cotton genomic nucleic acid marker selected from the group comprising SEQ ID NOs: 1-38 and C) selecting from the population at least one cotton plant comprising at least one allele associated with RKN resistance. The population provided may be derived by crossing at least one RKN resistant cotton plant with at least one RKN sensitive plant to form a population.

In one aspect, the cotton plants selected by the methods of the present invention exhibit a resistant reaction rating to RKN of no worse than about 2.0 using indexing scale of 0-5, where 0 is nematode free plant and 5=100% roots with galls.

In one aspect, the method of the present invention further comprises the step (d) of assaying the selected cotton plant for resistance to a RKN disease inducing pathogen. In a further aspect, the genotype is determined by an assay which is selected from the group consisting of single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, and Flap Endonuclease-mediated assays. In a further aspect, the cotton genomic nucleic acid marker is SEQ ID NO: 33.

The present invention also provides for an elite cotton plant produced by: a) providing a population of cotton plants; b) genotyping at least one cotton plant in the population with respect to a cotton genomic nucleic acid marker selected from the group comprising SEQ ID NOs: 1-38; and c) selecting from the population at least one cotton plant comprising at least one allele associated with RKN resistance. The elite cotton plant of the present invention can exhibit a transgenic trait. The transgenic trait is selected from the group consisting of herbicide tolerance, increased yield, insect control, fungal disease resistance, virus resistance, nematode resistance, bacterial disease resistance, mycoplasma disease resistance, modified oils production, high oil production, high protein production, germination and/or seedling growth control, enhanced animal and human nutrition, low raffinose, environmental stress resistance, increased digestibility, improved processing traits, improved flavor, nitrogen fixation, hybrid seed production, and reduced allergenicity. The herbicide tolerance can be selected from the group consisting of glyphosate, dicamba, glufosinate, sulfonylurea, bromoxynil, 2,4, Dichlorophenoxyacetic acid, and norflurazon herbicides.

The present invention further provides a method of introgressing at least one RKN resistance allele into a cotton plant comprising a) providing a population of cotton plants, b) screening the population with at least one nucleic acid marker, c) selecting from the population one or more cotton plants comprising one or more alleles associated with RKN resistance. In one aspect, the selected cotton plants exhibit a resistant reaction rating to RKN of no worse than about 2.0. The present invention further provides for a cotton plant produced by a) providing a population of cotton plants, b) screening the population with at least one nucleic acid marker, c) selecting from the population one or more cotton plants comprising one or more alleles associated with RKN resistance.

The invention further provides a substantially purified nucleic acid molecule for the detection of loci related to RKN resistance comprising a nucleic acid molecule selected from the group consisting of SEQ ID NOs: 1-62 and complements thereof. The invention further provides an isolated nucleic acid molecule for detecting a molecular marker representing a polymorphism in cotton DNA, wherein the nucleic acid molecule comprises at least 15 nucleotides that include or are adjacent to the polymorphism, wherein the nucleic acid molecule is at least 90 percent identical to a sequence of the same number of consecutive nucleotides in either strand of DNA that include or are adjacent to the polymorphism, and wherein the molecular marker is selected from the group consisting of SEQ ID NOs: 1-38. In one aspect, the isolated nucleic acid further comprises a detectable label or provides for incorporation of a detectable label. In a further aspect, the detectable label is selected from the group consisting of an isotope, a fluorophore, an oxidant, a reductant, a nucleotide and a hapten.

The present invention further provides a set of oligonucleotides comprising a) a pair of oligonucleotide primers wherein each of the primers comprises at least 12 contiguous nucleotides and wherein the pair of primers permit PCR amplification of a DNA segment comprising a molecular marker selected from the group consisting of SEQ ID NOs: 1-38 and b) at least one detector oligonucleotide that permits detection of a polymorphism in the amplified segment, wherein the sequence of the detector oligonucleotide is at least 95 percent identical to a sequence of the same number of consecutive nucleotides in either strand of a segment of cotton DNA that include or are adjacent to the polymorphism of step (a).

BRIEF DESCRIPTION OF THE NUCLEIC ACIDS

SEQ ID NO: 1 is a genomic sequence derived from *Gossypium hirsutum* associated with RKN resistance locus on Chromsome 11.

SEQ ID NO: 2 is a genomic sequence derived from *Gossypium hirsutum* associated with RKN resistance locus on Chromsome 11.

SEQ ID NO: 3 is a genomic sequence derived from *Gossypium hirsutum* associated with RKN resistance locus on Chromsome 11.

SEQ ID NO: 4 is a genomic sequence derived from *Gossypium hirsutum* associated with RKN resistance locus on Chromsome 11.

SEQ ID NO: 5 is a genomic sequence derived from *Gossypium hirsutum* associated with RKN resistance locus on Chromsome 11.

SEQ ID NO: 6 is a genomic sequence derived from *Gossypium hirsutum* associated with RKN resistance locus on Chromsome 11.

SEQ ID NO: 7 is a genomic sequence derived from *Gossypium hirsutum* associated with RKN resistance locus on Chromsome 11.

SEQ ID NO: 8 is a genomic sequence derived from *Gossypium hirsutum* associated with RKN resistance locus on Chromsome 11.

SEQ ID NO: 9 is a genomic sequence derived from *Gossypium hirsutum* associated with RKN resistance locus on Chromsome 11.

SEQ ID NO: 10 is a genomic sequence derived from *Gossypium hirsutum* associated with RKN resistance locus on Chromsome 11.

SEQ ID NO: 11 is a genomic sequence derived from *Gossypium hirsutum* associated with RKN resistance locus on Chromsome 11.

SEQ ID NO: 12 is a genomic sequence derived from *Gossypium hirsutum* associated with RKN resistance locus on Chromsome 11.

SEQ ID NO: 13 is a genomic sequence derived from *Gossypium hirsutum* associated with RKN resistance locus on Chromsome 11.

SEQ ID NO: 14 is a genomic sequence derived from *Gossypium hirsutum* associated with RKN resistance locus on Chromsome 11.

SEQ ID NO: 15 is a genomic sequence derived from *Gossypium hirsutum* associated with RKN resistance locus on Chromsome 11.

SEQ ID NO: 16 is a genomic sequence derived from *Gossypium hirsutum* associated with RKN resistance locus on Chromsome 11.

SEQ ID NO: 17 is a genomic sequence derived from *Gossypium hirsutum* associated with RKN resistance locus on Chromsome 11.

SEQ ID NO: 18 is a genomic sequence derived from *Gossypium hirsutum* associated with RKN resistance locus on Chromsome 11.

SEQ ID NO: 19 is a genomic sequence derived from *Gossypium hirsutum* associated with RKN resistance locus on Chromsome 11.

SEQ ID NO: 20 is a genomic sequence derived from *Gossypium hirsutum* associated with RKN resistance locus on Chromsome 11.

SEQ ID NO: 21 is a genomic sequence derived from *Gossypium hirsutum* associated with RKN resistance locus on Chromsome 11.

SEQ ID NO: 22 is a genomic sequence derived from *Gossypium hirsutum* associated with RKN resistance locus on Chromsome 11.

SEQ ID NO: 23 is a genomic sequence derived from *Gossypium hirsutum* associated with RKN resistance locus on Chromsome 11.

SEQ ID NO: 24 is a genomic sequence derived from *Gossypium hirsutum* associated with RKN resistance locus on Chromsome 11.

SEQ ID NO: 25 is a genomic sequence derived from *Gossypium hirsutum* associated with RKN resistance locus on Chromsome 11.

SEQ ID NO: 26 is a genomic sequence derived from *Gossypium hirsutum* associated with RKN resistance locus on Chromsome 11.

SEQ ID NO: 27 is a genomic sequence derived from *Gossypium hirsutum* associated with RKN resistance locus on Chromsome 11.

SEQ ID NO: 28 is a genomic sequence derived from *Gossypium hirsutum* associated with RKN resistance locus on Chromsome 11.

SEQ ID NO: 29 is a genomic sequence derived from *Gossypium hirsutum* associated with RKN resistance locus on Chromsome 11.

SEQ ID NO: 30 is a genomic sequence derived from *Gossypium hirsutum* associated with RKN resistance locus on Chromsome 11.

SEQ ID NO: 31 is a genomic sequence derived from *Gossypium hirsutum* associated with RKN resistance locus on Chromsome 11.

SEQ ID NO: 32 is a genomic sequence derived from *Gossypium hirsutum* associated with RKN resistance locus on Chromsome 11.

SEQ ID NO: 33 is a genomic sequence derived from *Gossypium hirsutum* associated with RKN resistance locus on Chromsome 11.

SEQ ID NO: 34 is a genomic sequence derived from *Gossypium hirsutum* associated with RKN resistance locus on Chromsome 11.

SEQ ID NO: 35 is a genomic sequence derived from *Gossypium hirsutum* associated with RKN resistance locus on Chromsome 11.

SEQ ID NO: 36 is a genomic sequence derived from *Gossypium hirsutum* associated with RKN resistance locus on Chromsome 11.

SEQ ID NO: 37 is a genomic sequence derived from *Gossypium hirsutum* associated with RKN resistance locus on Chromsome 11.

SEQ ID NO: 38 is a genomic sequence derived from *Gossypium hirsutum* associated with RKN resistance locus on Chromsome 11.

SEQ ID NO: 39 is a forward PCR primer for the amplification of SEQ ID NO: 33.

SEQ ID NO: 40 is a reverse PCR primer for the amplification of SEQ ID NO: 33.

SEQ ID NO: 41 is a forward PCR primer for the amplification of SEQ ID NO: 36.

SEQ ID NO: 42 is a reverse PCR primer for the amplification of SEQ ID NO: 36.

SEQ ID NO: 43 is a forward PCR primer for the amplification of SEQ ID NO: 9.

SEQ ID NO: 44 is a reverse PCR primer for the amplification of SEQ ID NO: 9.

SEQ ID NO: 45 is a probe for detecting the RKN resistance locus of SEQ ID NO: 33.

SEQ ID NO: 46 is a second probe for detecting the RKN resistance locus of SEQ ID NO: 34.

SEQ ID NO: 47 is a probe for detecting the RKN resistance locus of SEQ ID NO: 36.

SEQ ID NO: 48 is a second probe for detecting the RKN resistance locus of SEQ ID NO: 36.

SEQ ID NO: 49 is a probe for detecting the RKN resistance locus of SEQ ID NO: 9.

SEQ ID NO: 50 is a second probe for detecting the RKN resistance locus of SEQ ID NO: 9.

SEQ ID NO: 51 is a forward single base extension probe for detecting the RKN resistance locus of SEQ ID NO: 33.

SEQ ID NO: 52 is a reverse single base extension probe for detecting the RKN resistance locus of SEQ ID NO: 33.

SEQ ID NO: 53 is a forward single base extension probe for detecting the RKN resistance locus of SEQ ID NO: 36.

SEQ ID NO: 54 is a reverse single base extension probe for detecting the RKN resistance locus of SEQ ID NO: 36.

SEQ ID NO: 55 is a forward single base extension probe for detecting the RKN resistance locus of SEQ ID NO: 9.

SEQ ID NO: 56 is a reverse single base extension probe for detecting the RKN resistance locus of SEQ ID NO: 9.

SEQ ID NO: 57 is a hybridization probe for detecting the RKN resistance locus of SEQ ID NO: 33.

SEQ ID NO: 58 is a second hybridization probe for detecting the RKN resistance locus of SEQ ID NO: 33.

SEQ ID NO: 59 is a hybridization probe for detecting the RKN resistance locus of SEQ ID NO: 36.

SEQ ID NO: 60 is a second hybridization probe for detecting the RKN resistance locus of SEQ ID NO: 36.

SEQ ID NO: 61 is a hybridization probe for detecting the RKN resistance locus of SEQ ID NO: 9.

SEQ ID NO: 62 is a second hybridization probe for detecting the RKN resistance locus of SEQ ID NO: 9.

SEQ ID NO: 63 is a genomic sequence derived from *Gossypium hirsutum* associated with RKN resistance locus on Chromsome 7.

SEQ ID NO: 64 is a genomic sequence derived from *Gossypium hirsutum* associated with RKN resistance locus on Chromsome 7.

SEQ ID NO: 65 is a genomic sequence derived from *Gossypium hirsutum* associated with RKN resistance locus on Chromsome 7.

SEQ ID NO: 66 is a genomic sequence derived from *Gossypium hirsutum* associated with RKN resistance locus on Chromsome 7.

SEQ ID NO: 67 is a genomic sequence derived from *Gossypium hirsutum* associated with RKN resistance locus on Chromsome 7.

SEQ ID NO: 68 is a genomic sequence derived from *Gossypium hirsutum* associated with RKN resistance locus on Chromsome 7.

SEQ ID NO: 69 is a genomic sequence derived from *Gossypium hirsutum* associated with RKN resistance locus on Chromsome 7.

SEQ ID NO: 70 is a genomic sequence derived from *Gossypium hirsutum* associated with RKN resistance locus on Chromsome 7.

SEQ ID NO: 71 is a genomic sequence derived from *Gossypium hirsutum* associated with RKN resistance locus on Chromsome 7.

SEQ ID NO: 72 is a genomic sequence derived from *Gossypium hirsutum* associated with RKN resistance locus on Chromsome 7.

SEQ ID NO: 73 is a genomic sequence derived from *Gossypium hirsutum* associated with RKN resistance locus on Chromsome 7.

SEQ ID NO: 74 is a genomic sequence derived from *Gossypium hirsutum* associated with RKN resistance locus on Chromsome 7.

SEQ ID NO: 75 is a genomic sequence derived from *Gossypium hirsutum* associated with RKN resistance locus on Chromsome 7.

SEQ ID NO: 76 is a genomic sequence derived from *Gossypium hirsutum* associated with RKN resistance locus on Chromsome 7.

SEQ ID NO: 77 is a genomic sequence derived from *Gossypium hirsutum* associated with RKN resistance locus on Chromsome 7.

SEQ ID NO: 78 is a genomic sequence derived from *Gossypium hirsutum* associated with RKN resistance locus on Chromsome 7.

SEQ ID NO: 79 is a genomic sequence derived from *Gossypium hirsutum* associated with RKN resistance locus on Chromsome 7.

SEQ ID NO: 80 is a genomic sequence derived from *Gossypium hirsutum* associated with RKN resistance locus on Chromsome 7.

SEQ ID NO: 81 is a genomic sequence derived from *Gossypium hirsutum* associated with RKN resistance locus on Chromsome 7.

SEQ ID NO: 82 is a genomic sequence derived from *Gossypium hirsutum* associated with RKN resistance locus on Chromsome 7.

SEQ ID NO: 83 is a genomic sequence derived from *Gossypium hirsutum* associated with RKN resistance locus on Chromsome 7.

SEQ ID NO: 84 is a genomic sequence derived from *Gossypium hirsutum* associated with RKN resistance locus on Chromsome 7.

SEQ ID NO: 85 is a genomic sequence derived from *Gossypium hirsutum* associated with RKN resistance locus on Chromsome 7.

SEQ ID NO: 86 is a genomic sequence derived from *Gossypium hirsutum* associated with RKN resistance locus on Chromsome 7.

SEQ ID NO: 87 is a genomic sequence derived from *Gossypium hirsutum* associated with RKN resistance locus on Chromsome 7.

SEQ ID NO: 88 is a genomic sequence derived from *Gossypium hirsutum* associated with RKN resistance locus on Chromsome 7.

SEQ ID NO: 89 is a genomic sequence derived from *Gossypium hirsutum* associated with RKN resistance locus on Chromsome 7.

SEQ ID NO: 90 is a genomic sequence derived from *Gossypium hirsutum* associated with RKN resistance locus on Chromsome 7.

SEQ ID NO: 91 is a genomic sequence derived from *Gossypium hirsutum* associated with RKN resistance locus on Chromsome 7.

SEQ ID NO: 92 is a forward PCR primer for the amplification of SEQ ID NO: 73.

SEQ ID NO: 93 is a reverse PCR primer for the amplification of SEQ ID NO: 73.

SEQ ID NO: 94 is a forward PCR primer for the amplification of SEQ ID NO: 74.

SEQ ID NO: 95 is a reverse PCR primer for the amplification of SEQ ID NO: 74.

SEQ ID NO: 96 is a forward PCR primer for the amplification of SEQ ID NO: 75.

SEQ ID NO: 97 is a reverse PCR primer for the amplification of SEQ ID NO: 75.

SEQ ID NO: 98 is a hybridization probe for detecting the RKN resistance locus of SEQ ID NO: 73.

SEQ ID NO: 99 is a second hybridization probe for detecting the RKN resistance locus of SEQ ID NO: 73.

SEQ ID NO: 100 is a hybridization probe for detecting the RKN resistance locus of SEQ ID NO: 74.

SEQ ID NO: 101 is a second hybridization probe for detecting the RKN resistance locus of SEQ ID NO: 74.

SEQ ID NO: 102 is a hybridization probe for detecting the RKN resistance locus of SEQ ID NO: 75.

SEQ ID NO: 103 is a second hybridization probe for detecting the RKN resistance locus of SEQ ID NO: 75.

DETAILED DESCRIPTION OF THE INVENTION

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes IX, Oxford University Press: New York, 2007. The nomenclature for DNA bases as set forth at 37 CFR §1.822 is used.

An "allele" refers to an alternative sequence at a particular locus; the length of an allele can be as small as 1 nucleotide base, but is typically larger.

A "locus" is a position on a genomic sequence that is usually found by a point of reference; e.g., a DNA sequence that is a gene, or part of a gene or intergenic region. The loci of this invention comprise one or more polymorphisms in a population; i.e., alternative alleles are present in some individuals.

As used herein, "polymorphism" means the presence of two or more variations of a nucleic acid sequence or nucleic acid feature at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, "marker" means a detectable characteristic that can be used to discriminate between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics. As used herein, "genetic marker" means polymorphic nucleic acid sequence or nucleic acid feature. A genetic marker may be represented by one or more particular variant sequences, or by a consensus sequence. In another sense, a "genetic marker" is an isolated variant or consensus of such a sequence.

As used herein, "marker assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "typing" refers to any method whereby the specific allelic form of a given cotton genomic polymorphism is determined. For example, a single nucleotide polymorphism (SNP) is typed by determining which nucleotide is present (i.e. an A, G, T, or C). Insertion/deletions (Indels) are determined by determining if the Indel is present. Indels can be typed by a variety of assays including, but not limited to, marker assays.

As used herein, the phrase "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "interrogation position" refers to a physical position on a solid support that can be queried to obtain genotyping data for one or more predetermined genomic polymorphisms.

As used herein, "consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

As used herein, the term "single nucleotide polymorphism," also referred to by the abbreviation "SNP," means a polymorphism at a single site wherein the polymorphism constitutes a single base pair change, an insertion of one or more base pairs, or a deletion of one or more base pairs.

As used herein, the term "haplotype" means a chromosomal region within a haplotype window defined by at least one polymorphic molecular marker. The unique marker fingerprint combinations in each haplotype window define individual haplotypes for that window. Further, changes in a haplotype, brought about by recombination for example, may result in the modification of a haplotype so that it comprises only a portion of the original (parental) haplotype operably linked to the trait, for example, via physical linkage to a gene, QTL, or transgene. Any such change in a haplotype would be included in our definition of what constitutes a haplotype so long as the functional integrity of that genomic region is unchanged or improved.

As used herein, the term "haplotype window" means a chromosomal region that is established by statistical analyses known to those of skill in the art and is in linkage disequilibrium. Thus, identity by state between two inbred individuals (or two gametes) at one or more molecular marker loci located within this region is taken as evidence of identity-by-descent of the entire region. Each haplotype window includes at least one polymorphic molecular marker. Haplotype windows can be mapped along each chromosome in the genome. Haplotype windows are not fixed per se and, given the ever-increasing density of molecular markers, this invention anticipates the number and size of haplotype windows to evolve, with the number of windows increasing and their respective sizes decreasing, thus resulting in an ever-increasing degree confidence in ascertaining identity by descent based on the identity by state at the marker loci.

As used herein, "genotype" means the genetic component of the phenotype, and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, "genotyping" means the process of assaying the alleles present at one or more specific loci in an attempt to measure the genetic variation between members of a species. Current methods of genotyping include PCR, DNA sequencing, and probe hybridization. SNPs are the most common type of genetic variation. A SNP is a single base pair mutation at a specific locus, usually consisting of two alleles As used herein, "phenotype" means the detectable characteristics of a cell or organism which can be influenced by genotype.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

As used herein, "chromosomal position" means a linear designation of sites within a chromosome or genome, based upon the various frequencies of recombination between genetic markers As used herein, "quantitative trait locus (QTL)" means a locus that controls to some degree numerically representable traits that are usually continuously distributed.

As used herein, "resistance allele" means the isolated nucleic acid sequence that includes the polymorphic allele associated with resistance to root knot nematode.

As used herein, "cotton" means *Gossypium hirsutum* and includes all plant varieties that can be bred with cotton, including wild cotton species. More specifically, cotton plants from the species *Gossypium hirsutum* and the subspecies *Gossypium hirsutum* L. can be genotyped using these compositions and methods. In an additional aspect, the cotton plant is from the group *Gossypium arboreum* L., otherwise known as tree cotton. In another aspect, the cotton plant is from the group *Gossypium barbadense* L., otherwise known as American pima or Egyptian cotton. In another aspect, the cotton plant is from the group *Gossypium herbaceum* L., otherwise known as levant cotton. *Gossypium* or cotton plants can include hybrids, inbreds, partial inbreds, or members of defined or undefined populations.

As used herein, the term "comprising" means "including but not limited to".

As used herein, the term "elite line" means any line that has resulted from breeding and selection for superior agronomic performance. Non-limiting examples of elite lines that are commercially available include DP 555 BG/RR, DP 445 BG/RR, DP 444 BG/RR, DP 454 BG/RR, DP 161 B2RF, DP 141 B2RF, DP 0924 B2RF, DP 0935 B2RF, DP 121 RF, DP 174 RF (Deltapine); ST5599BR, ST5242BR, ST4554B2RF, ST4498B2RF, ST5458B2RF (Stoneville); FM9058F, FM9180B2F, FM1880B2F, FM1740B2F (FiberMax); PHY485WRF, PHY375WRF, PHY745WRF (Acala)(PhytoGen); and MCSO423B2RF, MCS0508B2RF (Cotton States).

In the present invention, an RKN resistant locus is located on Chromosome A11 (RKN-1). SNP markers used to monitor the introgression of RKN-1 include those selected from the group consisting of SEQ ID NOs: 1-38. Illustrative RKN-1 SNP marker DNA sequence SEQ ID NO: 33 can be amplified using the primers indicated as SEQ ID NOs: 39 through 40 and detected with probes indicated as SEQ ID NOs: 45 through 46. Illustrative RKN-1 SNP marker DNA sequence SEQ ID NO: 36 can be amplified using the primers indicated as SEQ ID NOs: 41 through 42 and detected with probes indicated as SEQ ID NOs: 47 through 48. Illustrative RKN-1 SNP marker DNA sequence SEQ ID NO: 9 can be amplified using the primers indicated as SEQ ID NOs: 43 through 44 and detected with probes indicated as SEQ ID NOs: 49 through 50.

In the present invention an RKN resistant locus is located on Chromosome A07 (RKN-2). SNP markers used to monitor the introgression of RKN-2 include those selected from the group consisting of SEQ ID NOs: 63-91. Illustrative RKN-2 SNP marker DNA sequence SEQ ID NO: 73 can be amplified using the primers indicated as SEQ ID NOs: 92 through 93 and detected with probes indicated as SEQ ID NOs: 98 through 99. Illustrative RKN-2 SNP marker DNA sequence SEQ ID NO: 74 can be amplified using the primers indicated as SEQ ID NOs: 94 through 95 and detected with probes indicated as SEQ ID NOs: 100 through 101. Illustrative RKN-2 SNP marker DNA sequence SEQ ID NO: 75 can be amplified using the primers indicated as SEQ ID NOs: 96 through 97 and detected with probes indicated as SEQ ID NOs: 102 through 103.

The present invention also provides a cotton plant comprising a nucleic acid molecule selected from the group consisting of SEQ ID NOs: 1-38, fragments thereof, and complements of both. The present invention also provides a cotton plant comprising a nucleic acid molecule selected from the group consisting of SEQ ID NOs: 39 through 50, fragments thereof, and complements of both.

The present invention also provides a cotton plant comprising at least one RKN resistance loci. In one aspect, a cotton plant is provided comprising an RKN resistant locus of chromosome A11 (RKN-1). In an additional aspect, a cotton plant is provided comprising an RKN resistant locus of chromosome A07 (RKN-2). In a further aspect, a cotton plant is provided comprising both resistant alleles, RKN-1 and RKN-2, respectively. In all aspects such alleles may be homozygous or heterozygous.

As used herein, RKN refers to any RKN variant or isolate. A cotton plant of the present invention can be resistant to one or more nematodes capable of causing or inducing galls similar to RKN. In one aspect, the present invention provides plants resistant to RKN as well as methods and compositions for screening cotton plants for resistance or susceptibility to RKN, caused by the genus *Meloidogyne*. In a preferred aspect, the present invention provides methods and compositions for screening cotton plants for resistance or susceptibility to *Meloidogyne incognita*.

In one aspect, the plant is selected from the genus *Gossypium*. In another aspect, the plant is selected from the species *Gossypium hirsutum*. In a further aspect, the plant is selected from the subspecies *Gossypium hirsutum* L. In an additional aspect, the plant is from the group *Gossypium arboreum* L., otherwise known as tree cotton. In another aspect, the plant is from the group *Gossypium barbadense* L., otherwise known as American pima or Egyptian cotton. In another aspect, cotton plant is from the group *Gossypium herbaceum* L., otherwise known as levant cotton. *Gossypium* or cotton plants can include hybrids, inbreds, partial inbreds, or members of defined or undefined populations.

Plants of the present invention can be a cotton plant that is very resistant, resistant, substantially resistant, moderately-resistant, comparatively resistant, partially resistant, moderately susceptible, or susceptible.

In a preferred aspect, the present invention provides a cotton plant to be assayed for resistance or susceptibility to RKN by any method to determine whether a cotton plant is very resistant, resistant, substantially resistant, moderately resistant, comparatively resistant, partially resistant, moderately susceptible, or susceptible.

A galling index scale is used to rate plants as resistant or susceptible to RKN. Roots of plants are examined for number and size of galls and rated according to a 0 (no galls) to 5 (100% roots with galls) scale. The detailed description of indexing is as follows: 0 (no visible galls, healthy root system); 1 (1-2 galls, healthy root system); 2 (3-12 galls, small size galls more visible); 3 (13-30 galls, large size galls more visible on tap root); 4 (31-60 galls, severe galling with large gall size); 5 (over 60 galls, >75% roots with large galls, root system non-functional). In this aspect, the plants with a rating below 2 were considered as resistant plants.

In another aspect, the cotton plant can show a comparative resistance compared to a non-resistant control cotton plant. In this aspect, a control cotton plant will preferably be genetically similar except for the RKN resistance allele or alleles in question. Such plants can be grown under similar conditions with equivalent or near equivalent exposure to the pathogen. In this aspect, the resistant plant or plants has less than 25%, 15%, 10%, 5%, 2% or 1% of leaf area infected.

A disease resistance QTL of the present invention may be introduced into an elite cotton inbred line. An "elite line" is any line that has resulted from breeding and selection for superior agronomic performance.

An RKN resistance QTL of the present invention may also be introduced into an elite cotton plant comprising one or more transgenes conferring herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in cotton.

A disease resistant QTL allele or alleles can be introduced from any plant that contains that allele (donor) to any recipient cotton plant. In one aspect, the recipient cotton plant can contain additional RKN resistant loci. In another aspect, the recipient cotton plant can contain a transgene. In another aspect, while maintaining the introduced QTL, the genetic contribution of the plant providing the disease resistant QTL can be reduced by back-crossing or other suitable approaches. In one aspect, the nuclear genetic material derived from the donor material in the cotton plant can be less than or about 50%, less than or about 25%, less than or about 13%, less than or about 5%, 3%, 2% or 1%, but that genetic material contains the cotton resistant locus or loci of interest.

It is further understood that a cotton plant of the present invention may exhibit the characteristics of any relative maturity group. In an aspect, the maturity group is selected from the group consisting of early maturing varieties, mid season maturing varieties, and full season varieties.

An allele of a QTL can, of course, comprise multiple genes or other genetic factors even within a contiguous genomic region or linkage group, such as a haplotype. As used herein, an allele of a disease resistance locus can therefore encompass more than one gene or other genetic factor where each individual gene or genetic component is also capable of exhibiting allelic variation and where each gene or genetic factor is also capable of eliciting a phenotypic effect on the quantitative trait in question. In an aspect of the present invention the allele of a QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in the present in the invention can denote a haplotype within a haplotype window wherein a phenotype can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular RKN locus or for a particular polymorphic marker.

The present invention also provides for parts of the plants of the present invention. Plant parts, without limitation, include seed, endosperm, ovule and pollen. In a particularly preferred aspect of the present invention, the plant part is a seed.

The present invention also provides a container of cotton in which greater than 50%, 60%, 70%, 80%, 90%, 95%, or 99% of the seeds comprising RKN resistance loci.

The container of cotton seeds can contain any number, weight, or volume of seeds. For example, a container can contain at lest, or greater than, about 10, 25, 50, 100, 200, 300, 400, 500, 600, 700, 80, 90, 1000, 1500, 2000, 2500, 3000, 3500, 4000 or more seeds. In another aspect, a container can contain about, or greater than about, 1 gram, 5 grams, 10 grams, 15 grams, 20 grams, 25 grams, 50 grams, 100 grams, 250 grams, 500 grams, or 1000 grams of seeds. Alternatively, the container can contain at least, or greater than, about 0 ounces, 1 ounce, 5 ounces, 10 ounces, 1 pound, 2 pounds, 3 pounds, 4 pounds, 5 pounds, 10 pounds, 15 pounds, 20 pounds, 25 pounds, or 50 pounds or more seeds.

Containers of cotton seeds can be any container available in the art. For example, a container can be a box, a bag, a can, a packet, a pouch, a tape roll, a pail, or a tube.

In another aspect, the seeds contained in the containers of cotton seeds can be treated or untreated cotton seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

Various patent and non-patent publications are cited herein, the disclosures of each of which are incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Phenotypic Rating Scale

To asses the reaction of plants to RKN, cotton plants were grown in growth chambers and artificially inoculated with 2,500 nematode eggs approximately 7 days after emergence. Plant roots were examined for galling 45-50 days after inoculation. A galling index of 0 (no galls) to 5 (100% roots with galls) was used to rate the plants. Table 1 provides the phenotypic rating scale used to identify RKN reaction in cotton plants.

TABLE 1

Phenotypic Rating Scale Used for RKN Reaction

| Rating | Phenotypic Description |
|---|---|
| 0 | No visible galls; healthy root system |
| 1 | 1-2 galls; healthy root system |
| 2 | 3-12 galls; small gall size |
| 3 | 13-30 galls; large size galls more visible on tap root |
| 4 | 31-60 galls; severe galling with large gall size |
| 5 | >60 galls; severe galling with >75% roots with large galls; root system nonfunctional |

Example 2

Identification of SNP Markers Associated with RKN Resistance

A mapping population was developed from the cross of the RKN resistant parent M240 with RKN susceptible parent 33B. A total of 250 near-isogenic lines (NILs) were developed for the mapping population. Ten replicates of each line were evaluated for reaction to RKN as described in Example 1.

Eleven SNP markers located on Chromosome A11 were used to screen the NIL mapping population. Of these, SNP marker NG0204877 was found to be highly associated with RKN resistance. Of 248 lines screened, the mean galling index of lines with the TT genotype was significantly lower than those with the AA genotype. Table 2 provides the mean galling index for lines with the genotype AA, AT, and TT. A t-test analysis was performed and the p-value for no mean difference between AA and TT genotypes on the galling index was $3.84 \times 10^{-82}$. The marker NG0204877 is on Chromosome A11 at position 181.1.

TABLE 2

Marker NG0204877 (SEQ ID NO. 31) is Associated with RKN Resistance in Cotton.

| Genotype | Mean Galling Index | Number of Lines |
|---|---|---|
| AA | 4.5 | 78 |
| AT | 3.0 | 37 |
| TT | 1.1 | 133 |

Example 3

Use of SNP markers for Monitoring RKN Resistance

Additional SNP markers are located on Chromosome A11. Table 3 provides the marker names, chromosome position, and the position of the polymorphism in the marker, and alleles.

In a breeding program, one or more markers provided in Table 3 can be used to select for and to introgress RKN resistance into a cotton plant. A cotton breeder can select one or more markers which are polymorphic between parents in a breeding cross to select progeny with the genotype of the RKN resistant parent.

TABLE 3

SNP Markers on Chromosome A11 for Detecting RKN Resistance.

| Marker | SEQ ID NO: | Chromosome Position | SNP Position[1] | Allele 1 | Allele 2 |
|---|---|---|---|---|---|
| NG0204212 | 1 | 142.5 | 303 | A | C |
| NG0204865 | 2 | 143 | 367 | A | G |
| NG0203354 | 3 | 145 | 253 | A | G |
| NG0207959 | 4 | 145.9 | 333 | A | T |
| NG0204475 | 5 | 147 | 382 | A | G |
| NG0210892 | 6 | 150.7 | 323 | C | T |
| NG0206447 | 7 | 150.7 | 447 | A | G |
| NG0209829 | 8 | 150.7 | 149 | A | C |
| NG0210628 | 9 | 150.7 | 171 | A | G |
| NG0203550 | 10 | 152.2 | 253 | G | T |
| NG0204129 | 11 | 158.4 | 325 | C | G |
| NG0209314 | 12 | 159.2 | 272 | A | T |
| NG0209936 | 13 | 159.8 | 62 | A | G |
| NG0207838 | 14 | 160.1 | 385 | A | G |
| NG0209012 | 15 | 160.1 | 59 | A | T |
| NG0209914 | 16 | 160.1 | 520 | A | T |
| NG0210596 | 17 | 160.1 | 107 | A | C |
| NG0207455 | 18 | 160.8 | 220 | G | * |
| NG0203802 | 19 | 163.6 | 122 | A | G |
| NG0207423 | 20 | 163.9 | 449 | C | T |
| NG0206483 | 21 | 165.5 | 209 | A | G |
| NG0209848 | 22 | 165.7 | 310 | C | G |
| NG0204309 | 23 | 166.4 | 125 | A | C |
| NG0206578 | 24 | 169.8 | 254 | A | T |
| NG0211496 | 25 | 171.2 | 188 | A | G |
| NG0206531 | 26 | 171.3 | 354 | C | T |
| NG0204091 | 27 | 172.2 | 143 | C | T |
| NG0210467 | 28 | 174.4 | 381 | A | G |
| NG0209154 | 29 | 178.5 | 221 | C | T |
| NG0210828 | 30 | 180.1 | 356 | A | G |
| NG0208423 | 31 | 180.1 | 166 | A | T |
| NG0208500 | 32 | 180.1 | 219 | C | T |
| NG0204877 | 33 | 181.1 | 409 | A | T |
| NG0210025 | 34 | 181.2 | 255 | A | G |
| NG0210010 | 35 | 182.2 | 192 | G | T |
| NG0209086 | 36 | 182.4 | 525 | C | G |
| NG0206691 | 37 | 183.5 | 218 | A | T |
| NG0208147 | 38 | 183.5 | 322 | A | G |

"*"Indicates a single nucleotide Deletion
[1]SNP Position: refers to the position of the SNP polymorphism in the indicated SEQ ID NO.

TABLE 3A

SNP Markers on Chromosome A07 for Detecting RKN Resistance.

| Marker | SEQ ID NO: | Chromosome Position | SNP Position[1] | Allele 1 | Allele 2 |
|---|---|---|---|---|---|
| NG0203799 | 63 | 32.2 | 268 | T | A |
| NG0210921 | 64 | 33.1 | 190 | G | A |
| NG0210441 | 65 | 34.7 | 356 | G | A |
| NG0210456 | 66 | 35.2 | 139 | T | G |
| NG0204031 | 67 | 40.3 | 50 | G | A |
| NG0207405 | 68 | 41.1 | 143 | T | C |
| NG0210569 | 69 | 45.3 | 443 | T | G |
| NG0206553 | 70 | 45.7 | 194 | G | C |
| NG0210273 | 71 | 46.0 | 359 | T | C |
| NG0208436 | 72 | 46.6 | 85 | G | C |
| NG0206957 | 73 | 47.5 | 384 | T | G |
| NG0207837 | 74 | 47.5 | 142 | G | A |
| NG0207518 | 75 | 47.8 | 506 | T | C |
| NG0211237 | 76 | 47.8 | 439 | T | C |
| NG0210755 | 77 | 48.1 | 173 | T | A |
| NG0208863 | 78 | 48.5 | 348 | T | A |
| NG0203306 | 79 | 49.0 | 376 | G | A |
| NG0210314 | 80 | 49.5 | 489 | G | A |
| NG0208128 | 81 | 50.3 | 180 | G | A |
| NG0209149 | 82 | 50.8 | 108 | T | A |
| NG0209751 | 83 | 52.7 | 64 | G | A |
| NG0204353 | 84 | 53.2 | 338 | T | C |
| NG0209136 | 85 | 58.8 | 563 | C | A |
| NG0207947 | 86 | 62.2 | 554 | T | C |

TABLE 3A-continued

SNP Markers on Chromosome A07 for Detecting RKN Resistance.

| Marker | SEQ ID NO: | Chromosome Position | SNP Position[1] | Allele 1 | Allele 2 |
|---|---|---|---|---|---|
| NG0204860 | 87 | 64.6 | 540 | C | A |
| NG0207151 | 88 | 64.6 | 148 | G | A |
| NG0208606 | 89 | 64.6 | 150 | G | A |
| NG0206706 | 90 | 68.6 | 487 | G | A |
| NG0207731 | 91 | 71.6 | 169 | T | C |

[1]SNP Position: refers to the position of the SNP polymorphism in the indicated SEQ ID NO.

Example 4

Exemplary Marker Assays for Detecting RKN Resistance

In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. Exemplary primers and probes for amplifying and detecting genomic regions associated with cotton RKN resistance are given in Table 4.

TABLE 4

Exemplary Assays for Detecting RKN Resistance

| Marker | Marker SEQ ID | SNP Position | SEQ ID Forward Primer | SEQ ID Reverse Primer | SEQ ID Probe 1 | SEQ ID Probe 2 |
|---|---|---|---|---|---|---|
| NG0204877 | 33 | 409 | 39 | 40 | 45 | 46 |
| NG0208147 | 36 | 322 | 41 | 42 | 47 | 48 |
| NG0204129 | 9 | 325 | 43 | 44 | 49 | 50 |

Example 5

Oligonucleotide Probes Useful for Detecting Cotton Plants with RKN Resistance Loci by Single Base Extension Methods Oligonucleotides can also be used to detect or type the polymorphisms associated with RKN resistance disclosed herein by single base extension (SBE)-based SNP detection methods. Exemplary oligonucleotides for use in SBE-based SNP detection are provided in Table 5. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in Table 4 in the columns labeled "Forward Primer SEQ ID" and "Reverse Primer SEQ ID". Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected. Exemplary forward and reverse SBE probes are provided in Table 5.

TABLE 5

Probes (Extension Primers) for Single Base Extension (SBE) Assays

| Marker | Marker SEQ ID NO. | SNP Position | Probe (SBE) | Probe SEQ ID NO. |
|---|---|---|---|---|
| NG0204877 | 33 | 409 | TGATAACGGGATTTATT | 51 |
| NG0204877 | 33 | 409 | GATCAATCCGATGAACA | 52 |
| NG0208147 | 36 | 322 | ATTAAATGAAAAACGGG | 53 |
| NG0208147 | 36 | 322 | GAGGTTTTATTACAACA | 54 |
| NG0204129 | 9 | 325 | TACTGTCTCCTTGTAGA | 55 |
| NG0204129 | 9 | 325 | TAGAGGCAATTAAAGAA | 56 |

Example 6

Oligonucleotide Hybridization Probes Useful for Detecting Cotton Plants with RKN Resistance Loci Oligonucleotides can also be used to detect or type the polymorphisms associated with RKN resistance disclosed herein by hybridization-based SNP detection methods. Oligonucleotides capable of hybridizing to isolated nucleic acid sequences which include the polymorphism are provided. It is within the skill of the art to design assays with experimentally determined stringency to discriminate between the allelic states of the polymorphisms presented herein. Exemplary assays include Southern blots, Northern blots, microarrays, in situ hybridization, and other methods of polymorphism detection based on hybridization. Exemplary oligonucleotides for use in hybridization-based SNP detection are provided in Table 6. These oligonucleotides can be detectably labeled with radioactive labels, fluorophores, or other chemiluminescent means to facilitate detection of hybridization to samples of genomic or amplified nucleic acids derived from one or more cotton plants using methods known in the art.

TABLE 6

Oligonucleotide hybridization probes

| Marker | Marker SEQ ID NO. | SNP Position | Hybridization Probe | Probe SEQ ID NO. |
|---|---|---|---|---|
| NG0204877 | 33 | 409 | TTTATTAGTGTTCATC | 57 |
| NG0204877 | 33 | 409 | TTTATTTGTGTTCATC | 58 |

TABLE 6-continued

Oligonucleotide hybridization probes

| Marker | Marker SEQ ID NO. | SNP Position | Hybridization Probe | Probe SEQ ID NO. |
|---|---|---|---|---|
| NG0208147 | 36 | 322 | AACGGGATGTTGTAA | 59 |
| NG0208147 | 36 | 322 | AACGGGAATGTTGTAA | 60 |
| NG0204129 | 9 | 325 | TGTAGAGCTTCTTTAA | 61 |
| NG0204129 | 9 | 325 | TGTAGACCTTCTTTAA | 62 |

Example 7

Prophetic Example of Introgression of RKN Resistance Using SNP Markers

A plant breeder can use SNP markers to facilitate the introgression of the RKN resistance locus on Chromosome A11 and to select for lines carrying the favorable alleles for one or more of said SNP markers. In this example, the cotton line M240 is used as a donor of RKN resistance. The SNP marker NG0204877 (SEQ ID NO: 31) is used to monitor the introgression of the RKN resistance locus. A plant breeder can select the favorable genotype as provided in Table 2 to select plants for RKN resistance arising from the donor while selecting for the recipient genome in adjacent chromosome regions. In practice, this reduces the amount of linkage drag from the donor genome that maybe associated with undesirable agronomic or fiber quality properties.

The introgression of one or more resistance loci is achieved via repeated backcrossing to a recurrent parent accompanied by selection to retain one or more RKN resistance loci from the donor parent. This backcrossing procedure is implemented at any stage in line development and occurs in conjunction with breeding for superior agronomic characteristics or one or more traits of interest, including transgenic and nontransgenic traits.

Alternatively, a forward breeding approach is employed wherein one or more RKN resistance loci can be monitored for successful introgression following a cross with a susceptible parent with subsequent generations genotyped for one or more RKN resistance loci and for one or more additional traits of interest, including transgenic and nontransgenic traits.

Example 8

Introgression of RKN-1 and RKN-2 Using SNP markers to Produce a Cotton Plant Resistant to Root Knot Nematode A plant breeder can use SNP markers to facilitate the introgression of the RKN-1 resistant locus on Chromosome A07 and the RKN-2 resistant locus on Chromosome A11 to select for lines carrying the favorable alleles for one or more of said SNP markers. In this example, the cotton line M-315 is used as a donor of RKN resistance. The SNP marker N00204877 (SEQ ID NO: 31) was used to monitor the introgression of the RKN-1 resistant locus and the SNP markers NG0206957 (SEQ ID NO: 73), NG0207837 (SEQ ID NO: 74), and NG0207518 (SEQ ID NO: 75) were used to monitor the introgression of the RKN-2 resistance locus. A plant breeder can select the favorable polymorphic genotype as provided in to select plants for RKN resistance arising from the donor while selecting for the recipient genome in adjacent chromosome regions. In practice, this reduces the amount of linkage drag from the donor genome that maybe associated with undesirable agronomic or fiber quality properties.

The introgression of one or more resistance loci is achieved via repeated backcrossing to a recurrent parent accompanied by selection to retain one or more RKN resistance loci from the donor parent. This backcrossing procedure is implemented at any stage in line development and occurs in conjunction with breeding for superior agronomic characteristics or one or more traits of interest, including transgenic and nontransgenic traits.

Alternatively, a forward breeding approach is employed wherein one or more RKN resistance loci can be monitored for successful introgression following a cross with a susceptible parent with subsequent generations genotyped for one or more RKN resistance loci and for one or more additional traits of interest, including transgenic and nontransgenic traits.

In view of the foregoing, it will be seen that the several advantages of the invention are achieved and attained. The embodiments were chosen and described in order to best explain the principles of the invention and its practical application to thereby enable others skilled in the art to best utilize the invention in various embodiments and with various modifications as are suited to the particular use contemplated.

Various patent and non-patent publications are cited herein, the disclosures of each of which are, to the extent necessary, incorporated herein by reference in their entireties. As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

The invention claimed is:

1. A method for selecting a cotton plant comprising in its genome the root knot nematode resistance loci RKN-1 and RKN-2, comprising the steps of:
 a. providing a population of cotton plants;
 b. genotyping at least one cotton plant from said population with respect to the RKN-1 locus using at least one SNP marker selected from Table 3 and with respect to the RKN-2 locus using at least one SNP marker selected from Table 3A; and
 c. selecting a cotton plant comprising a desirable genotype at each of the RKN-1 locus and the RKN-2 locus, wherein said desirable genotype confers resistance to root knot nematode in said identified cotton plant.

2. The method of claim 1, wherein the population is derived by crossing at least one root knot nematode resistant cotton plant with at least one other cotton plant to form a population.

3. The method of claim 1, further comprising exposing the selected cotton plant to a root knot nematode inducing pathogen.

4. The method of claim 3, wherein the selected cotton plant exhibits a root knot nematode resistance reaction rating of no worse than about 2.0.

5. The method of claim 1, wherein said at least one SNP marker selected from Table 3 is NG0204877.

6. The method of claim 1, wherein said at least one SNP marker selected from Table 3A are NG0206957, NG0207837, and NG0207518.

7. The method of claim 1, wherein the population of cotton plants exhibit a transgenic trait.

8. The method of claim 7, wherein the transgenic trait is selected from the group consisting of herbicide tolerance, increased yield, insect control, fungal disease resistance, virus resistance, nematode resistance, bacterial disease resistance, mycoplasma disease resistance, modified oils production, high oil production, high protein production, germination and/or seedling growth control, enhanced animal and human nutrition, low raffinose, environmental stress resistance, increased digestibility, improved processing traits, improved flavor, nitrogen fixation, hybrid seed production, and reduced allergenicity.

9. The method of claim 1, wherein said genotyping comprises detection of a locus comprising a nucleic acid molecule comprising the sequence of SEQ ID NO: 6 (NG0210892), SEQ ID NO:8 (NG0209829), SEQ ID NO:9 (NG0210628), SEQ ID NO:12 (NG0209314), SEQ ID NO:13 (NG0209936), SEQ ID NO:15 (NG0209012), SEQ ID NO:16 (NG0209914), SEQ ID NO:17 (NG0210596), SEQ ID NO:22 (NG0209848), SEQ ID NO:25 (NG0211496), SEQ ID NO:28 (NG0210467), SEQ ID NO:29 (NG0209154), SEQ ID NO:30 (NG0210828), SEQ ID NO:31 (NG0208423), SEQ ID NO:32 (NG0208500), SEQ ID NO:34 (NG0210025), SEQ ID NO:35 (NG0210010), SEQ ID NO:36 (NG0209086), SEQ ID NO:64 (NG0210921), SEQ ID NO:65 (NG0210441), SEQ ID NO:66 (NG0210456), SEQ ID NO:69 (NG0210569), SEQ ID NO:71 (NG0210273), SEQ ID NO:72 (NG0208436), SEQ ID NO:76 (NG0211237), SEQ ID NO:77 (NG0210755), SEQ ID NO:78 (NG0208863), SEQ ID NO:80 (NG0210314), SEQ ID NO:81 (NG0208128), SEQ ID NO:82 (NG0209149), SEQ ID NO:83 (NG0209751), SEQ ID NO:85 (NG0209136), or SEQ ID NO:89 (NG0208606).

* * * * *